(12) United States Patent
Curran et al.

(10) Patent No.: US 7,776,049 B1
(45) Date of Patent: Aug. 17, 2010

(54) SPINAL IMPLANT INSERTER, IMPLANT, AND METHOD

(75) Inventors: Matthew Curran, Carlsbad, CA (US); Eric Kovach, Carlsbad, CA (US); Dan Ahlgren, Poway, CA (US); Bryan Hildebrand, Whitefish, MT (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 10/264,307

(22) Filed: Oct. 2, 2002

(51) Int. Cl.
  *A61B 17/58* (2006.01)
  *A61F 2/00* (2006.01)
(52) U.S. Cl. .................................................. 606/99
(58) Field of Classification Search ............. 623/11.11, 623/16.11, 17.11–17.16; 606/60, 61, 99
  See application file for complete search history.

(56) References Cited

U.S. PATENT DOCUMENTS

| | | | |
|---|---|---|---|
| 3,486,505 A | 12/1969 | Morrison | |
| 3,518,993 A | 7/1970 | Blake | |
| 3,604,487 A | 9/1971 | Gilbert | |
| 3,745,995 A | 7/1973 | Kraus | 128/82.1 |
| 3,848,601 A | 11/1974 | Ma et al. | 128/305 |
| 4,026,304 A | 5/1977 | Levy | 128/419 |
| 4,026,305 A | 5/1977 | Brownlee et al. | 128/419 |
| 4,646,738 A | 3/1987 | Trott | 606/170 |
| 4,657,550 A | 4/1987 | Daher | 623/17 |
| 4,743,256 A | 5/1988 | Brantigan | 623/17 |
| 4,781,591 A | 11/1988 | Allen | |
| 4,834,757 A | 5/1989 | Brantigan | |
| 4,877,020 A | 10/1989 | Vich | 128/92 |
| 4,878,915 A | 11/1989 | Brantigan | 623/17 |
| 4,904,261 A * | 2/1990 | Dove et al. | 623/17.16 |
| 4,932,975 A | 6/1990 | Main et al. | 623/17 |
| 4,961,740 A | 10/1990 | Ray et al. | 606/61 |
| 4,962,766 A | 10/1990 | Herzon | 128/741 |
| 5,026,373 A | 6/1991 | Ray et al. | 606/61 |
| 5,055,104 A | 10/1991 | Ray | 606/61 |
| 5,062,845 A | 11/1991 | Kuslich et al. | 606/80 |
| 5,092,572 A | 3/1992 | Litwak et al. | 269/328 |
| 5,133,717 A | 7/1992 | Chopin | 606/61 |
| 5,133,755 A | 7/1992 | Brekke | 623/16 |
| 5,171,278 A | 12/1992 | Pisharodi | 623/17 |
| 5,192,327 A | 3/1993 | Brantigan | 623/17 |
| 5,217,497 A | 6/1993 | Mehdian | 623/17 |

(Continued)

FOREIGN PATENT DOCUMENTS

CA   2015507   1/1991

(Continued)

OTHER PUBLICATIONS

Alleyne, Cargill H., et al., "Current and future approaches to lumbar disc surgery: A literature review", *Medscape Orthopedics & Sports Medicine*, 1, [www.medscape.com/Medscape/OrthoSportsMed/1997/v01.n11/.../mos3057],(1997).

(Continued)

*Primary Examiner*—Anu Ramana
(74) *Attorney, Agent, or Firm*—Johnathan Spangler

(57) ABSTRACT

An improved implant inserter and implant where the inserter includes a set of prongs for gripping the implant and the implant includes a plurality of recesses for mating with the set of prongs.

29 Claims, 38 Drawing Sheets

U.S. PATENT DOCUMENTS

| | | | |
|---|---|---|---|
| 5,269,785 A | 12/1993 | Bonutti | 606/80 |
| 5,284,153 A | 2/1994 | Raymond et al. | 128/741 |
| 5,290,494 A | 3/1994 | Coombes et al. | 264/41 |
| 5,300,076 A | 4/1994 | Leriche | 606/73 |
| 5,304,210 A | 4/1994 | Crook | 607/51 |
| 5,306,307 A * | 4/1994 | Senter et al. | 623/17.16 |
| 5,306,309 A | 4/1994 | Wagner et al. | 623/17 |
| 5,322,505 A | 6/1994 | Krause et al. | 604/24 |
| 5,334,205 A | 8/1994 | Cain | |
| 5,336,223 A | 8/1994 | Rogers | 606/61 |
| 5,364,400 A | 11/1994 | Rego, Jr. et al. | 606/72 |
| 5,395,372 A | 3/1995 | Holt et al. | 606/61 |
| 5,397,363 A | 3/1995 | Gelbard | 623/17 |
| 5,405,391 A | 4/1995 | Henderson et al. | 623/17 |
| 5,413,602 A | 5/1995 | Metz-Stavenhagen | 623/17 |
| 5,425,772 A | 6/1995 | Brantigan | 623/17 |
| 5,431,658 A | 7/1995 | Moskovich | 606/99 |
| 5,443,514 A | 8/1995 | Steffee | 623/17 |
| 5,443,515 A | 8/1995 | Cohen et al. | 623/17 |
| 5,445,639 A | 8/1995 | Kuslich et al. | 606/80 |
| 5,454,811 A | 10/1995 | Huebner | 606/60 |
| 5,458,638 A | 10/1995 | Kuslich et al. | 623/17 |
| 5,484,403 A | 1/1996 | Yoakum et al. | 604/59 |
| 5,489,308 A | 2/1996 | Kuslich et al. | 623/17 |
| 5,522,879 A | 6/1996 | Scopelianos | 623/1 |
| 5,522,899 A | 6/1996 | Michelson | 623/17 |
| 5,524,624 A | 6/1996 | Tepper et al. | 128/660.3 |
| 5,527,312 A | 6/1996 | Ray | 606/61 |
| 5,534,030 A | 7/1996 | Navarro et al. | 623/17 |
| 5,540,688 A | 7/1996 | Navas | 606/61 |
| 5,545,222 A | 8/1996 | Bonutti | 623/11 |
| 5,554,191 A * | 9/1996 | Lahille et al. | 623/17.11 |
| 5,562,736 A | 10/1996 | Ray et al. | 623/17 |
| 5,565,005 A | 10/1996 | Erickson et al. | 607/51 |
| 5,571,190 A | 11/1996 | Ulrich | 623/17 |
| 5,571,192 A | 11/1996 | Schonhoffer | 623/17 |
| 5,593,409 A | 1/1997 | Michelson | 606/61 |
| 5,609,636 A | 3/1997 | Kohrs et al. | 623/17 |
| 5,611,800 A | 3/1997 | Davis et al. | 606/61 |
| 5,611,810 A | 3/1997 | Arnold et al. | 606/185 |
| 5,632,747 A | 5/1997 | Scarborough et al. | 606/79 |
| 5,645,598 A | 7/1997 | Brosnahan et al. | 623/17 |
| 5,653,761 A | 8/1997 | Pisharodi | 623/17 |
| 5,653,762 A | 8/1997 | Pisharodi | 623/17 |
| 5,658,336 A | 8/1997 | Pisharodi | 623/17 |
| 5,658,337 A | 8/1997 | Kohrs et al. | 623/17 |
| 5,662,710 A | 9/1997 | Bonutti | 623/11 |
| 5,665,122 A | 9/1997 | Kambin | 623/17 |
| 5,669,909 A | 9/1997 | Zdeblick et al. | 606/61 |
| 5,676,703 A | 10/1997 | Gelbard | 623/17 |
| 5,683,394 A | 11/1997 | Rinner | 606/86 |
| 5,683,400 A | 11/1997 | McGuire | 606/96 |
| 5,683,464 A | 11/1997 | Wagner et al. | 623/17 |
| 5,690,629 A | 11/1997 | Asher et al. | 606/61 |
| 5,700,264 A | 12/1997 | Zucherman et al. | 606/79 |
| 5,700,291 A | 12/1997 | Kuslich et al. | 623/17 |
| 5,700,292 A | 12/1997 | Marguiles | 623/17 |
| 5,702,449 A | 12/1997 | McKay | 623/17.16 |
| 5,702,451 A | 12/1997 | Biedermann et al. | 623/17 |
| 5,702,453 A | 12/1997 | Rabbe et al. | 623/17 |
| 5,702,454 A | 12/1997 | Baumgartner | 623/17 |
| 5,702,455 A | 12/1997 | Saggar | 623/17.15 |
| 5,703,451 A | 12/1997 | Yamamichi et al. | 318/492 |
| 5,707,373 A | 1/1998 | Sevrain et al. | 606/72 |
| 5,711,957 A | 1/1998 | Patat et al. | 424/224 |
| 5,716,415 A | 2/1998 | Steffee | 623/17 |
| 5,720,748 A | 2/1998 | Kuslich et al. | 606/80 |
| 5,720,751 A | 2/1998 | Jackson | 606/86 |
| 5,741,261 A | 4/1998 | Moscovitz et al. | 606/79 |
| 5,755,797 A | 5/1998 | Baumgartner | 623/17 |
| 5,766,252 A | 6/1998 | Henry et al. | 623/17 |
| 5,772,661 A | 6/1998 | Michelson | 606/61 |
| 5,775,331 A | 7/1998 | Raymond et al. | 128/741 |
| 5,779,642 A | 7/1998 | Nightengale | 600/461 |
| 5,782,830 A | 7/1998 | Farris | 606/61 |
| 5,782,919 A | 7/1998 | Zdeblick et al. | 623/17 |
| 5,785,710 A | 7/1998 | Michelson | 606/61 |
| 5,797,909 A | 8/1998 | Michelson | 606/61 |
| 5,800,549 A | 9/1998 | Bao et al. | 623/17 |
| 5,800,550 A | 9/1998 | Sertich | 623/17 |
| 5,814,084 A | 9/1998 | Grivas et al. | 623/16 |
| 5,851,208 A | 12/1998 | Trott | 606/80 |
| 5,865,845 A | 2/1999 | Thalgott | 623/17 |
| 5,865,848 A | 2/1999 | Baker | 623/17 |
| 5,885,299 A | 3/1999 | Winslow et al. | 606/99 |
| 5,888,219 A | 3/1999 | Bonutti | 623/11 |
| 5,888,224 A | 3/1999 | Beckers et al. | 623/17 |
| 5,893,890 A | 4/1999 | Pisharodi | 623/17 |
| 5,904,719 A | 5/1999 | Errico et al. | 623/17 |
| 5,910,315 A | 6/1999 | Stevenson et al. | 424/422 |
| 5,954,769 A | 9/1999 | Rosenlicht | 623/16 |
| 5,968,098 A | 10/1999 | Winslow | 623/17 |
| 5,993,474 A | 11/1999 | Ouchi | 606/206 |
| 6,004,326 A | 12/1999 | Castro et al. | 606/99 |
| 6,015,436 A | 1/2000 | Schunhuffer | 623/17 |
| 6,033,405 A | 3/2000 | Winslow et al. | 606/61 |
| 6,039,761 A | 3/2000 | Li et al. | 623/17 |
| 6,042,582 A | 3/2000 | Ray | 606/61 |
| 6,045,580 A | 4/2000 | Scarborough et al. | 623/17 |
| 6,048,342 A | 4/2000 | Zucherman et al. | 606/61 |
| 6,063,088 A | 5/2000 | Winslow | 606/61 |
| 6,083,225 A | 7/2000 | Winslow et al. | 606/61 |
| 6,096,080 A | 8/2000 | Nicholson et al. | 623/17 |
| 6,102,948 A | 8/2000 | Brosnahan, III | 623/17 |
| 6,120,506 A | 9/2000 | Kohrs et al. | 606/80 |
| 6,126,689 A * | 10/2000 | Brett | 623/17.16 |
| 6,132,472 A | 10/2000 | Bonutti | 623/23 |
| 6,136,031 A * | 10/2000 | Middleton | 623/17.16 |
| 6,159,211 A | 12/2000 | Boriani et al. | 606/61 |
| 6,159,215 A | 12/2000 | Urbahns et al. | 606/86 |
| 6,174,311 B1 * | 1/2001 | Branch et al. | 606/61 |
| 6,193,756 B1 | 2/2001 | Studer et al. | 623/17.15 |
| 6,200,347 B1 | 3/2001 | Anderson | 623/16.11 |
| 6,224,607 B1 | 5/2001 | Michelson | 606/96 |
| 6,224,631 B1 | 5/2001 | Kohrs | 623/17.11 |
| 6,241,769 B1 | 6/2001 | Nicholson et al. | 623/17.11 |
| 6,241,771 B1 | 6/2001 | Gresser et al. | 623/17.16 |
| 6,251,140 B1 | 6/2001 | Marino et al. | 623/17.16 |
| 6,258,125 B1 | 7/2001 | Paul et al. | 623/17.11 |
| 6,277,149 B1 | 8/2001 | Boyle et al. | 623/17.16 |
| 6,319,257 B1 | 11/2001 | Carignan et al. | 606/99 |
| 6,371,989 B1 | 4/2002 | Chauvin et al. | 623/17.11 |
| 6,440,142 B1 | 8/2002 | Ralph et al. | 606/99 |
| 6,442,814 B1 | 9/2002 | Landry et al. | 26/29 |
| 6,454,806 B1 | 9/2002 | Cohen et al. | 623/17.15 |
| 6,527,773 B1 | 3/2003 | Lin et al. | 606/61 |
| 6,595,998 B2 | 7/2003 | Johnson et al. | 606/90 |
| 6,610,065 B1 * | 8/2003 | Branch et al. | 606/84 |
| 6,635,086 B2 | 10/2003 | Lin | 623/17.11 |
| 6,648,895 B2 | 11/2003 | Burkus et al. | 606/90 |
| 6,695,882 B2 * | 2/2004 | Bianchi et al. | 623/17.16 |
| 6,719,794 B2 * | 4/2004 | Gerber et al. | 623/17.11 |
| 6,852,126 B2 | 2/2005 | Ahlgren | |
| 2002/0055781 A1 * | 5/2002 | Sazy | 623/17.11 |
| 2002/0058950 A1 | 5/2002 | Winterbottom et al. | |
| 2002/0065560 A1 * | 5/2002 | Varga et al. | 623/17.16 |
| 2002/0091447 A1 * | 7/2002 | Shimp et al. | 623/17.16 |
| 2002/0143400 A1 * | 10/2002 | Biscup | 623/17.11 |
| 2003/0105528 A1 | 6/2003 | Shimp et al. | |
| 2003/0149438 A1 * | 8/2003 | Nichols et al. | 606/99 |

| | | | |
|---|---|---|---|
| 2005/0149194 A1 | 7/2005 | Ahlgren | |

FOREIGN PATENT DOCUMENTS

| | | |
|---|---|---|
| EP | 369603 | 5/1990 |
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| FR | 2813519 A1 * | 3/2002 |
| WO | WO-91/06261 | 5/1991 |
| WO | WO-94/04100 | 3/1994 |
| WO | WO-94/10928 | 5/1994 |
| WO | WO-95/01810 | 1/1995 |
| WO | WO-96/08205 | 3/1996 |
| WO | WO-96/17564 | 3/1996 |
| WO | WO-96/41582 | 12/1996 |
| WO | WO-97/20513 | 6/1997 |
| WO | WO-97/33525 | 9/1997 |
| WO | WO-97/37620 | 10/1997 |
| WO | WO-98/09586 | 3/1998 |
| WO | WO-98/14142 | 4/1998 |
| WO | WO-98/17208 | 4/1998 |
| WO | WO-98/25539 | 6/1998 |
| WO | WO-99/08627 | 2/1999 |
| WO | WO-99/38461 | 8/1999 |
| WO | WO-00/45712 | 8/2000 |
| WO | WO-00/45713 | 8/2000 |
| WO | WO-01/41681 | 6/2001 |
| WO | WO-01/49333 | 7/2001 |

OTHER PUBLICATIONS

Benini, et al., "Undercutting decompression and posterior fusion with translaminar facet screw fixation in degenerative lumbar spinal stenosis: Technique and results", *Neuro-Orthopedics*, (1995),159-172.

Kambin, et al., "History and current status of percutaneous arthroscopic disc surgery", *Spine*, 21, (1996),57S-61S.

Stein, et al., "Percutaneous facet joint fusion: Preliminary experience", *Journal of Vascular and Interventional Radiology*, 4, (1993),69-74.

Vamvanij, et al., "Surgical treatment of internal disc disruption: An outcome study of four fusion techniques", *Journal of Spinal Disorders*, 4, (1998),375-382.

* cited by examiner

| SIZE TABLE 1 | |
|---|---|
| DESCRIPTION | DIMENSION H |
| B1 PORTAL XLIF ALLOGRAFT 6 X 9 X 20mm | .276 |
| B1 PORTAL XLIF ALLOGRAFT 8 X 9 X 20mm | .355 |
| B1 PORTAL XLIF ALLOGRAFT 10 X 9 X 20mm | .433 |
| B1 PORTAL XLIF ALLOGRAFT 12 X 9 X 20mm | .512 |
| B1 PORTAL XLIF ALLOGRAFT 14 X 9 X 20mm | .591 |
| B1 PORTAL XLIF ALLOGRAFT 16 X 9 X 20mm | .670 |

| SIZE TABLE 2 | |
|---|---|
| DESCRIPTION | DIMENSION H |
| B1 PORTAL XLIF ALLOGRAFT 6 X 11 X 20mm | .276 |
| B1 PORTAL XLIF ALLOGRAFT 8 X 11 X 20mm | .355 |
| B1 PORTAL XLIF ALLOGRAFT 10 X 11 X 20mm | .433 |
| B1 PORTAL XLIF ALLOGRAFT 12 X 11 X 20mm | .512 |
| B1 PORTAL XLIF ALLOGRAFT 14 X 11 X 20mm | .591 |
| B1 PORTAL XLIF ALLOGRAFT 16 X 11 X 20mm | .670 |

| SIZE TABLE 3 | |
|---|---|
| DESCRIPTION | DIMENSION H |
| B1 PORTAL XLIF ALLOGRAFT 6 X 9 X 25mm | .276 |
| B1 PORTAL XLIF ALLOGRAFT 8 X 9 X 25mm | .355 |
| B1 PORTAL XLIF ALLOGRAFT 10 X 9 X 25mm | .433 |
| B1 PORTAL XLIF ALLOGRAFT 12 X 9 X 25mm | .512 |
| B1 PORTAL XLIF ALLOGRAFT 14 X 9 X 25mm | .591 |
| B1 PORTAL XLIF ALLOGRAFT 16 X 9 X 25mm | .670 |

| SIZE TABLE 4 | |
|---|---|
| DESCRIPTION | DIMENSION H |
| B1 PORTAL XLIF ALLOGRAFT 6 X 11 X 25mm | .276 |
| B1 PORTAL XLIF ALLOGRAFT 8 X 11 X 25mm | .355 |
| B1 PORTAL XLIF ALLOGRAFT 10 X 11 X 25mm | .433 |
| B1 PORTAL XLIF ALLOGRAFT 12 X 11 X 25mm | .512 |
| B1 PORTAL XLIF ALLOGRAFT 14 X 11 X 25mm | .591 |
| B1 PORTAL XLIF ALLOGRAFT 16 X 11 X 25mm | .670 |

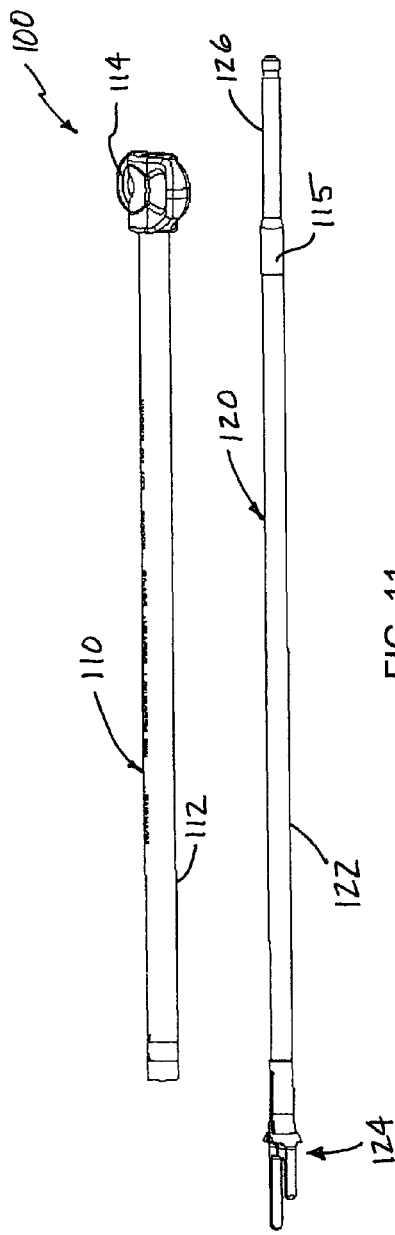
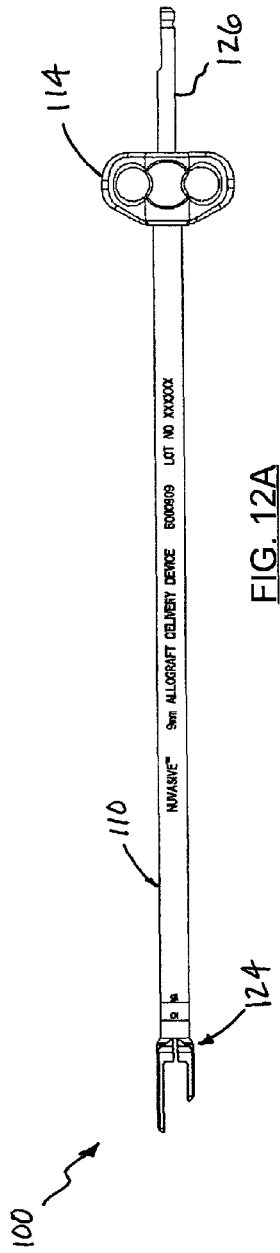
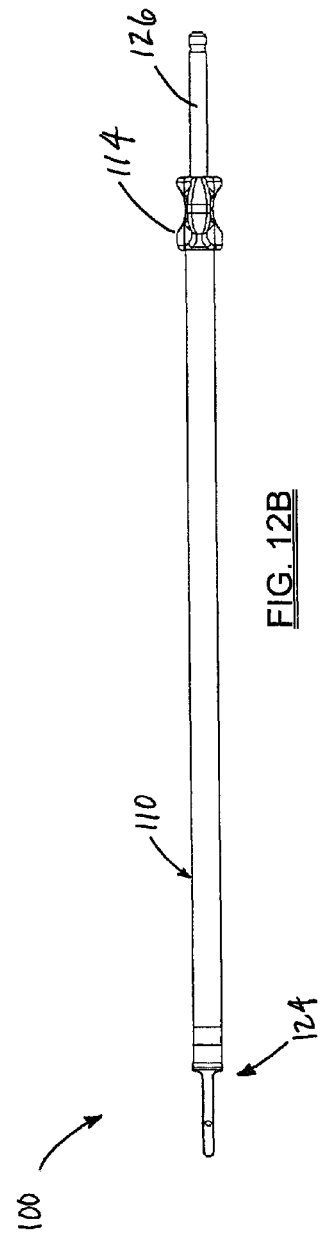
FIG. 11
FIG. 12A
FIG. 12B

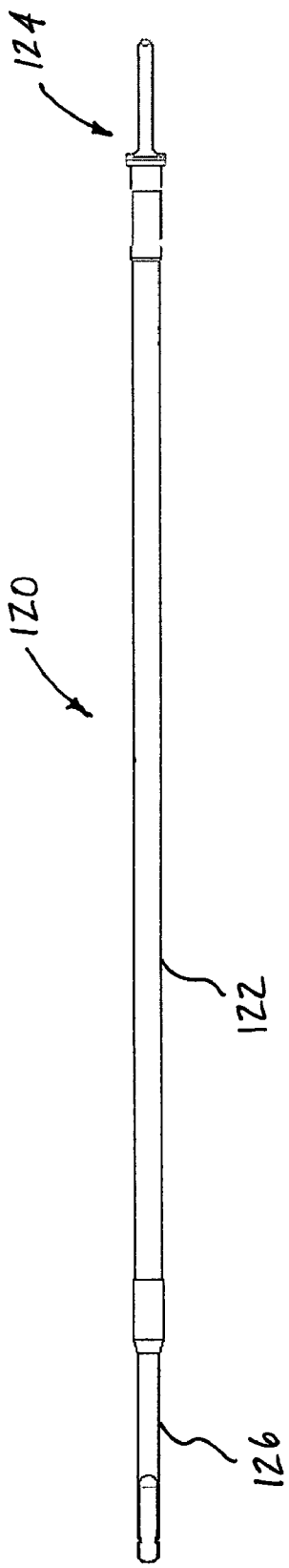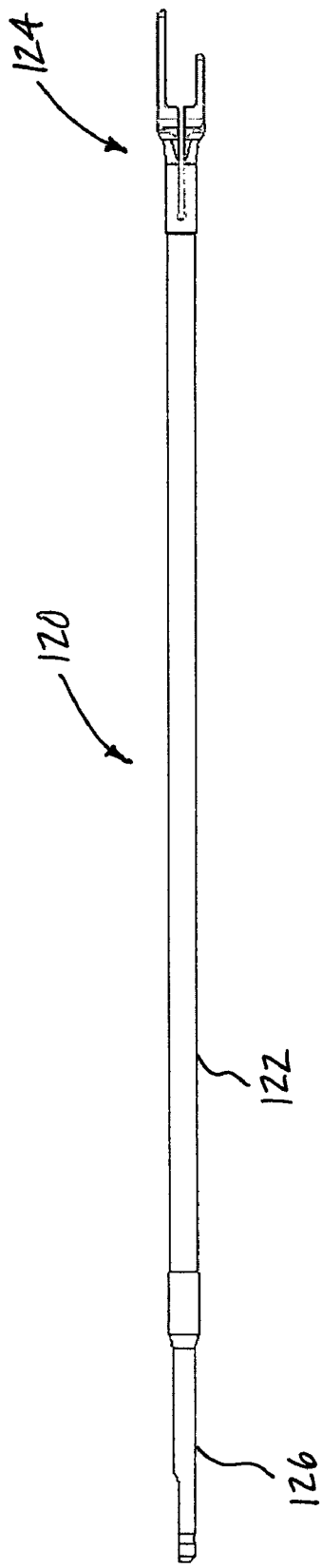
FIG. 13A
FIG. 13B

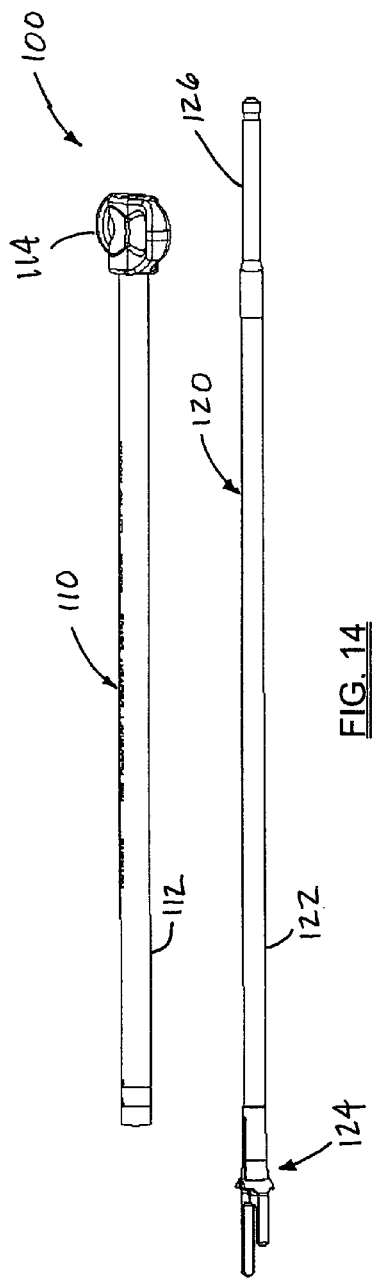
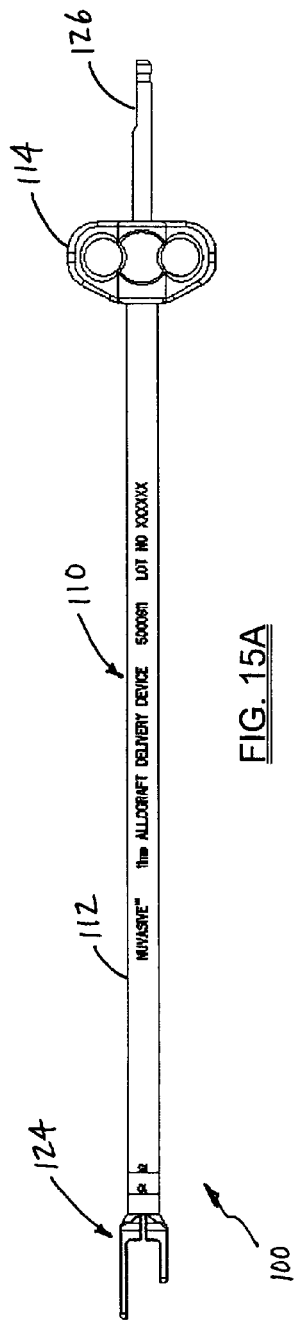
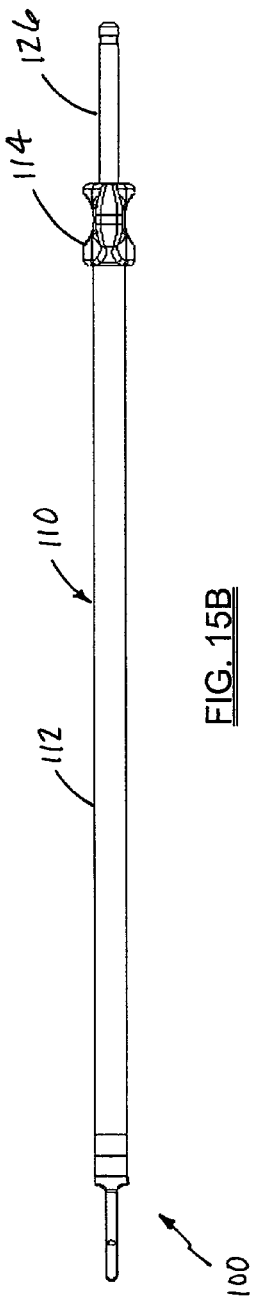
FIG. 14
FIG. 15A
FIG. 15B

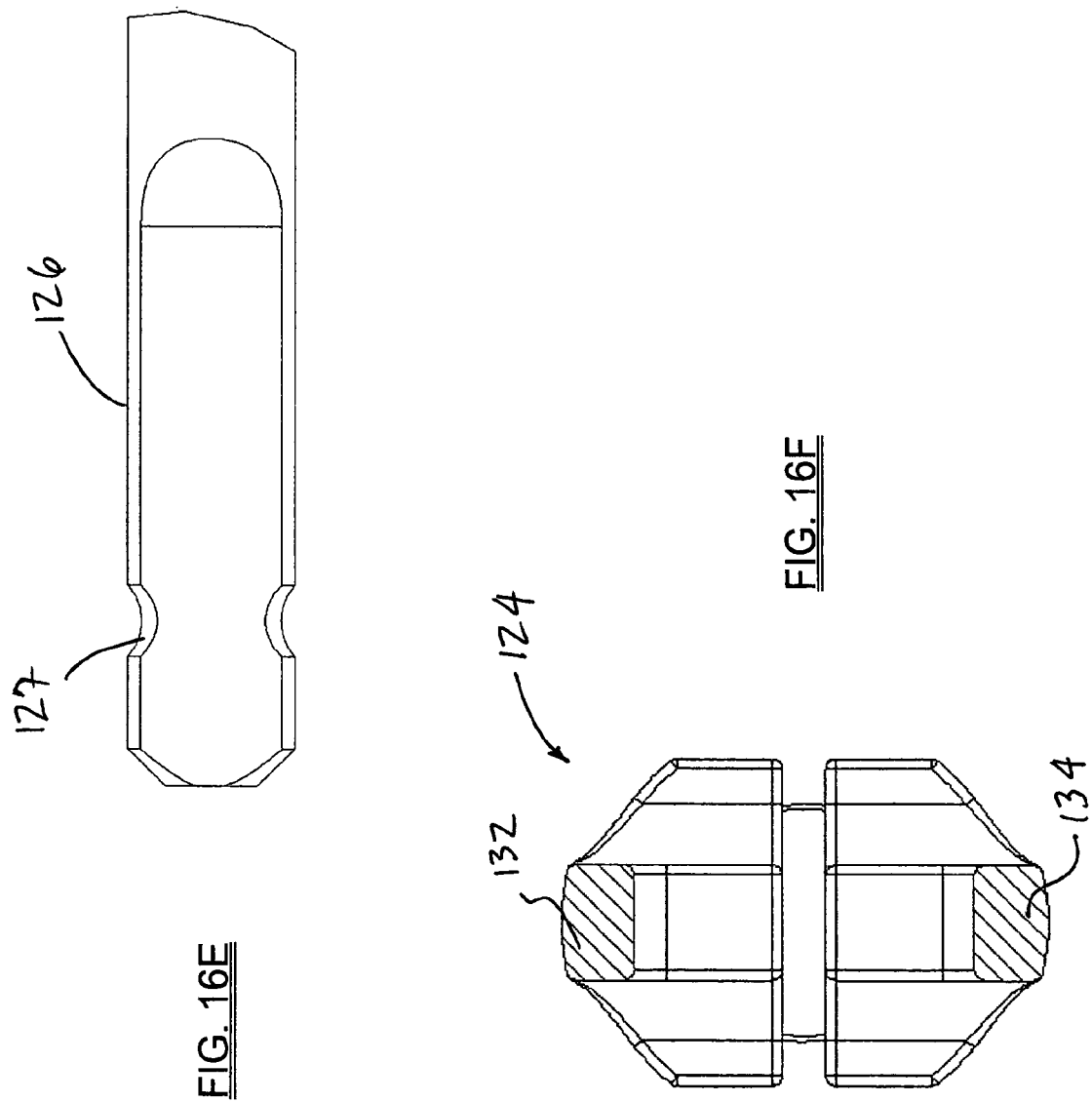

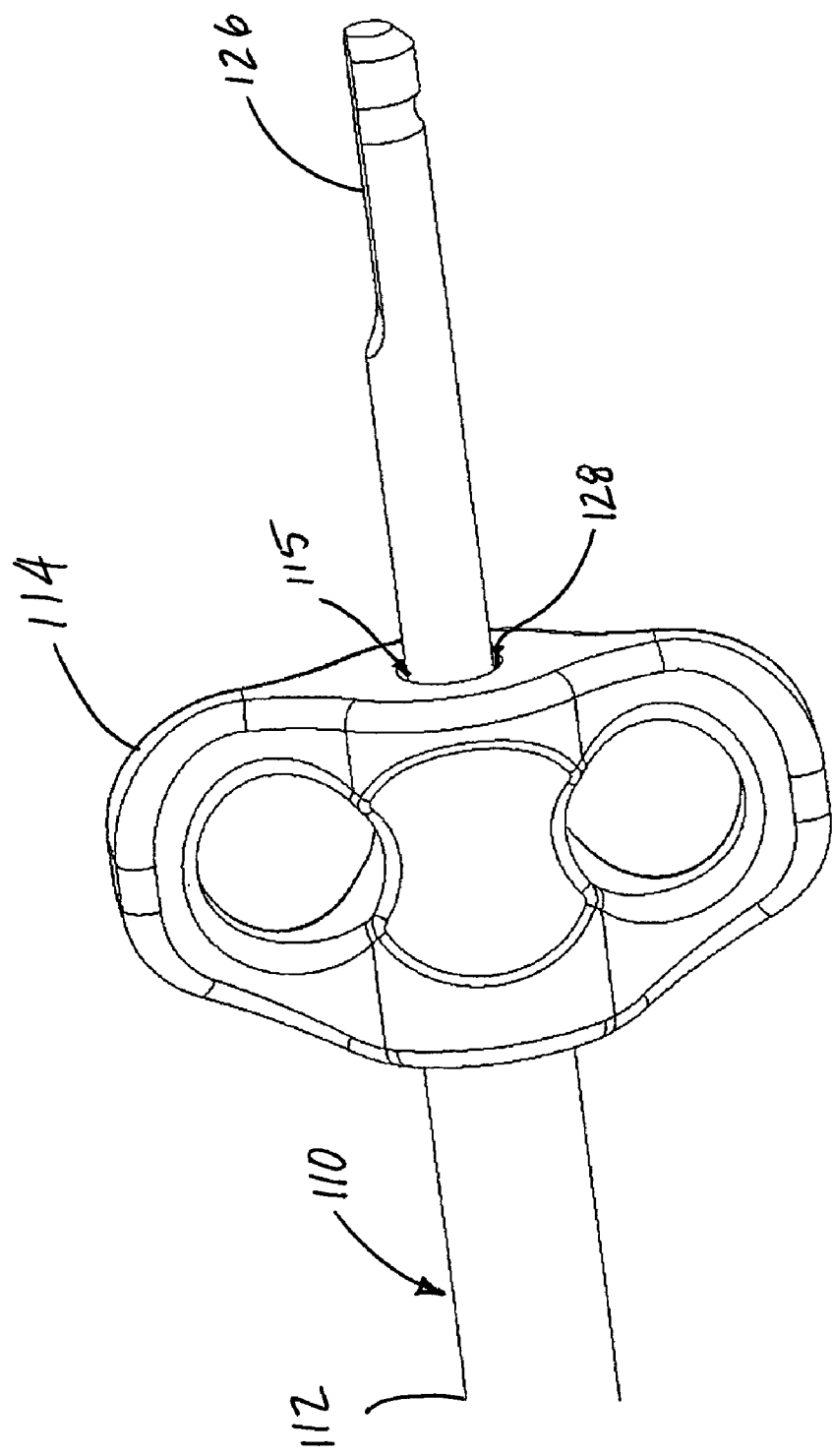

SPINAL IMPLANT INSERTER, IMPLANT, AND METHOD

BACKGROUND OF THE INVENTION

1. Field of the Invention

This invention relates to spinal implant insertion devices, implants, and methods, in particular to spinal intervetebral implant insertion devices, implants, and methods.

2. Description of Related Art

It is desirable to be able to insert one or more bony or prosthetic implants between vertebrae to stabilize the vertebrae or promote fusion of the vertebrae. Further, it is desirable to insert these implants via a minimally invasive procedure to reduce the potential trauma to a patient. In minimally invasive implant insertion procedures, it is desirable to be able to monitor the location of the implant relative to the vertebrae using a fluoroscope. When inserting bony implants, however, it may be difficult to visualize the implant via the fluoroscope. Accordingly, a need exists for an inserter, implant, and minimally invasive procedure that enables a surgeon to monitor the implant location relative to the vertebrae during the insertion process.

SUMMARY OF THE INVENTION

The present invention includes an improved spinal implant insertion device, implant, and minimally invasive spinal implant insertion procedure.

BRIEF DESCRIPTION OF THE DRAWINGS

FIG. 11 is a diagram of an exemplary 9 mm wide implant insertion tool in two parts, an exemplary collar and fork in accordance with the present invention.

FIG. 12A is a top view diagram of the exemplary 9 mm wide implant insertion tool in accordance with the present invention.

FIG. 12B is a side view diagram of the exemplary 9 mm wide implant insertion tool in accordance with the present invention.

FIG. 13A is a side view diagram of the exemplary 9 mm wide implant insertion tool fork in accordance with the present invention.

FIG. 13B is a top view diagram of the exemplary 9 mm wide implant insertion tool fork in accordance with the present invention.

FIG. 14 is a diagram of an exemplary 11 mm wide implant insertion tool in two parts, an exemplary collar and fork in accordance with the present invention.

FIG. 15A is a top view diagram of the exemplary 11 mm wide implant insertion tool in accordance with the present invention.

FIG. 15B is a side view diagram of the exemplary 11 mm wide implant insertion tool in accordance with the present invention.

FIG. 16E is a detailed side view diagram of the exemplary 11 mm wide implant insertion tool fork proximal end in accordance with the present invention.

FIG. 16F is a detailed end view diagram of the exemplary 11 mm wide implant insertion tool fork distal end in accordance with the present invention.

FIG. 21B is an isometric detailed cross-sectional view of the exemplary 9 mm wide implant insertion tool proximal end in accordance with the present invention.

DESCRIPTION OF THE SPECIFIC EMBODIEMENTS

Throughout this description, the preferred embodiment and examples shown should be considered as exemplars, rather than as limitations on the present invention.

Figure 1:
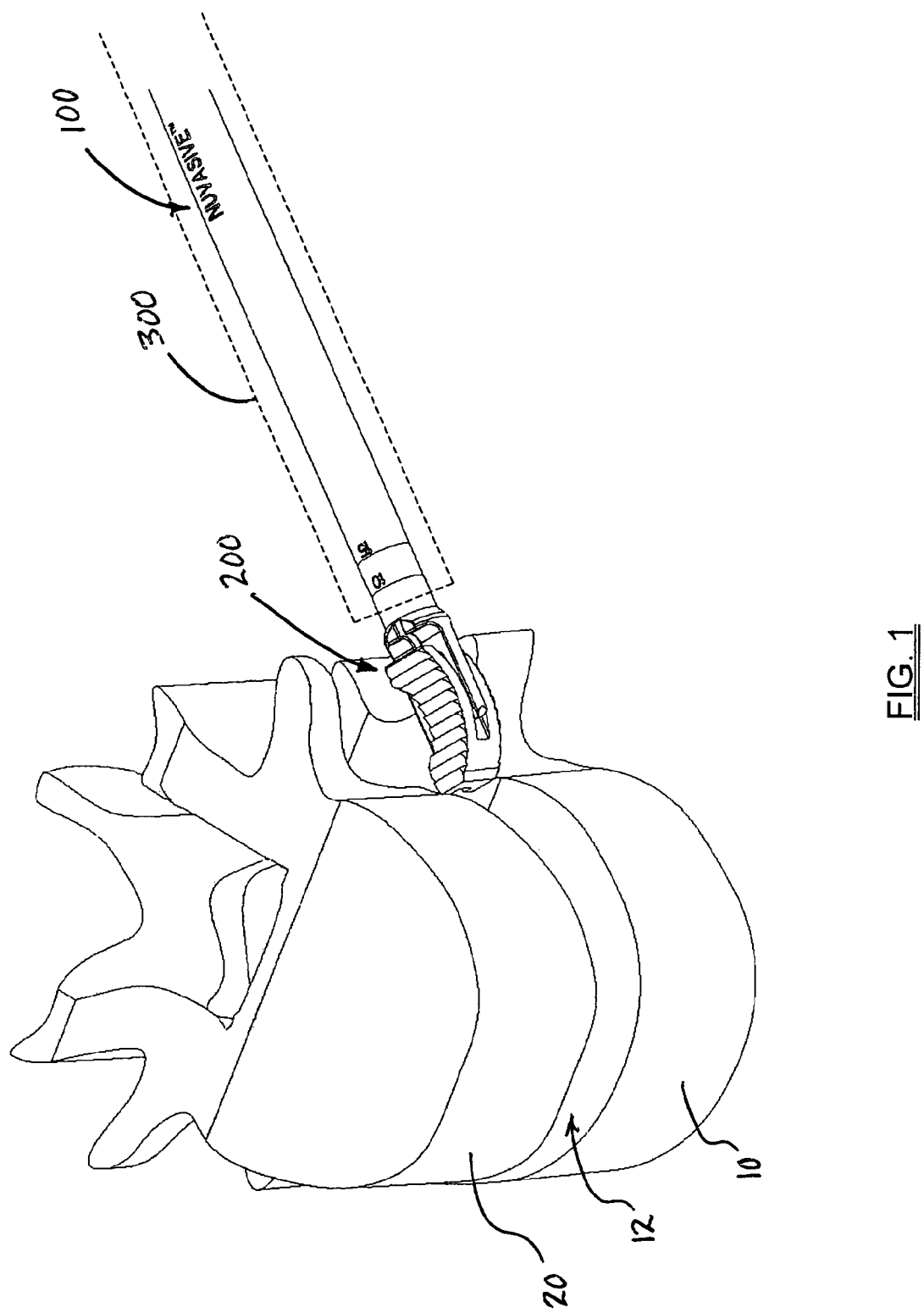
FIGS. 1-4 depict a cut-away view of an exemplary process of inserting an exemplary implant using an exemplary inserter in accordance with the present invention.
Figure 2:
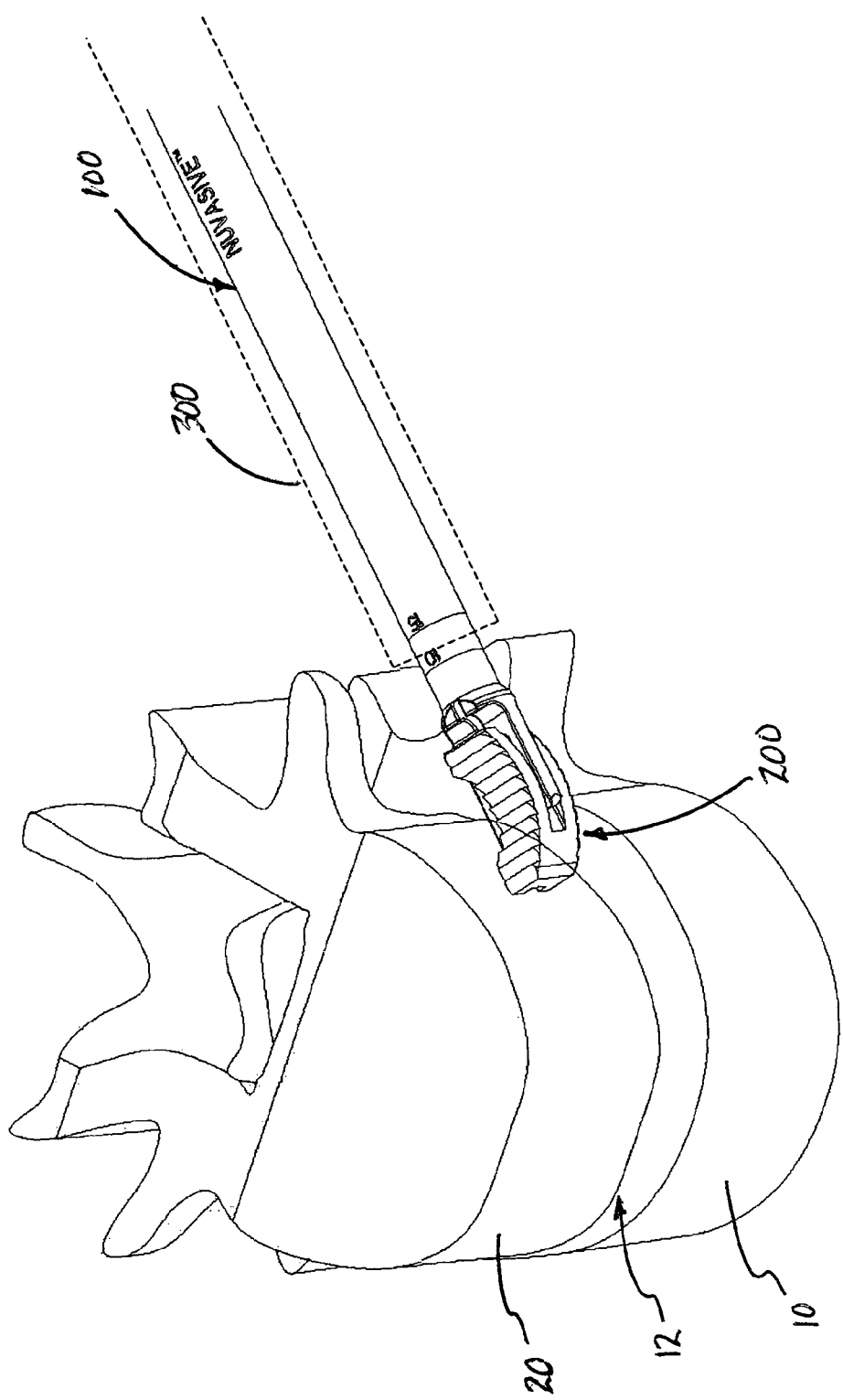
Figure 3:
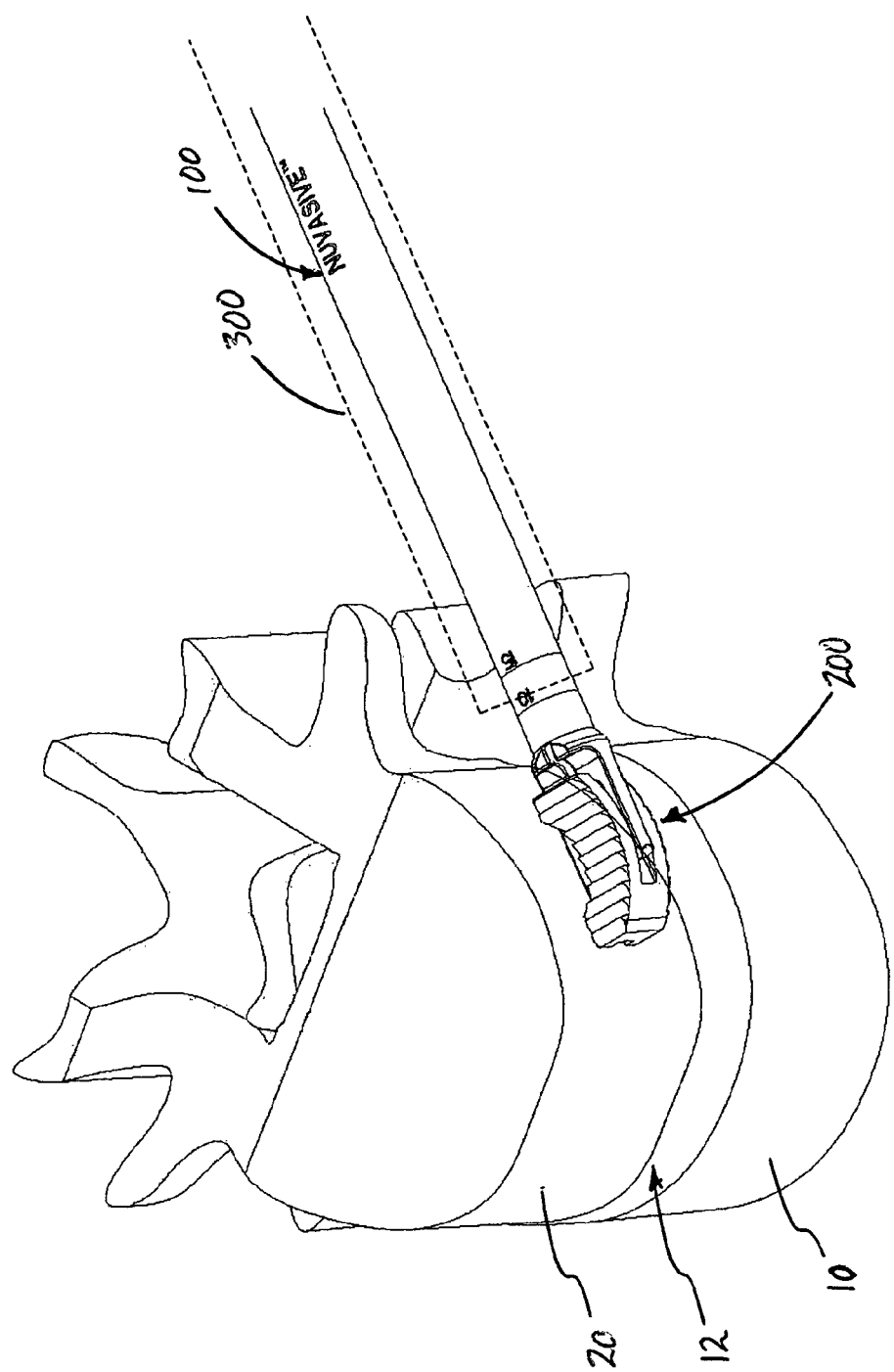
Figure 4:
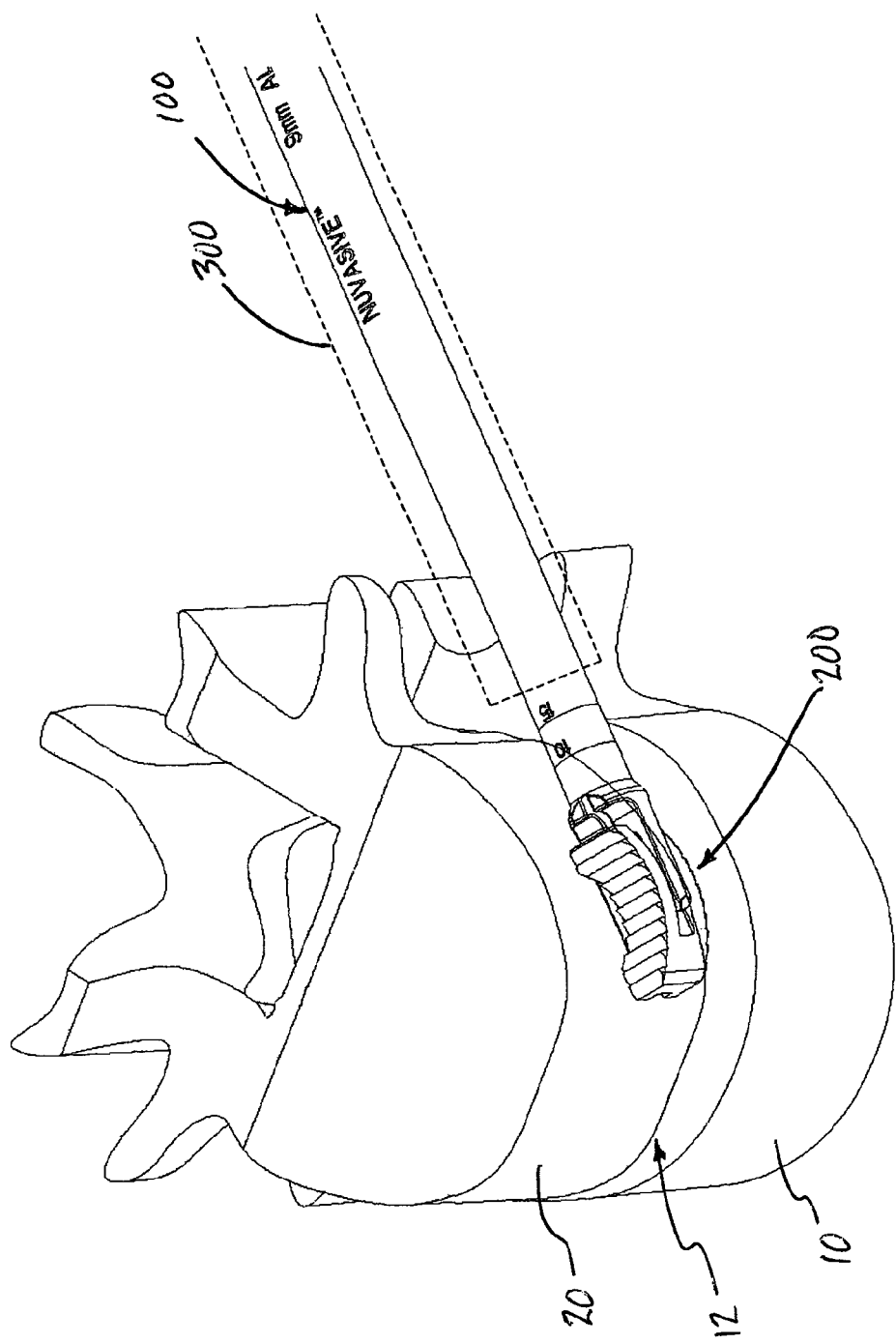
Figure 5:
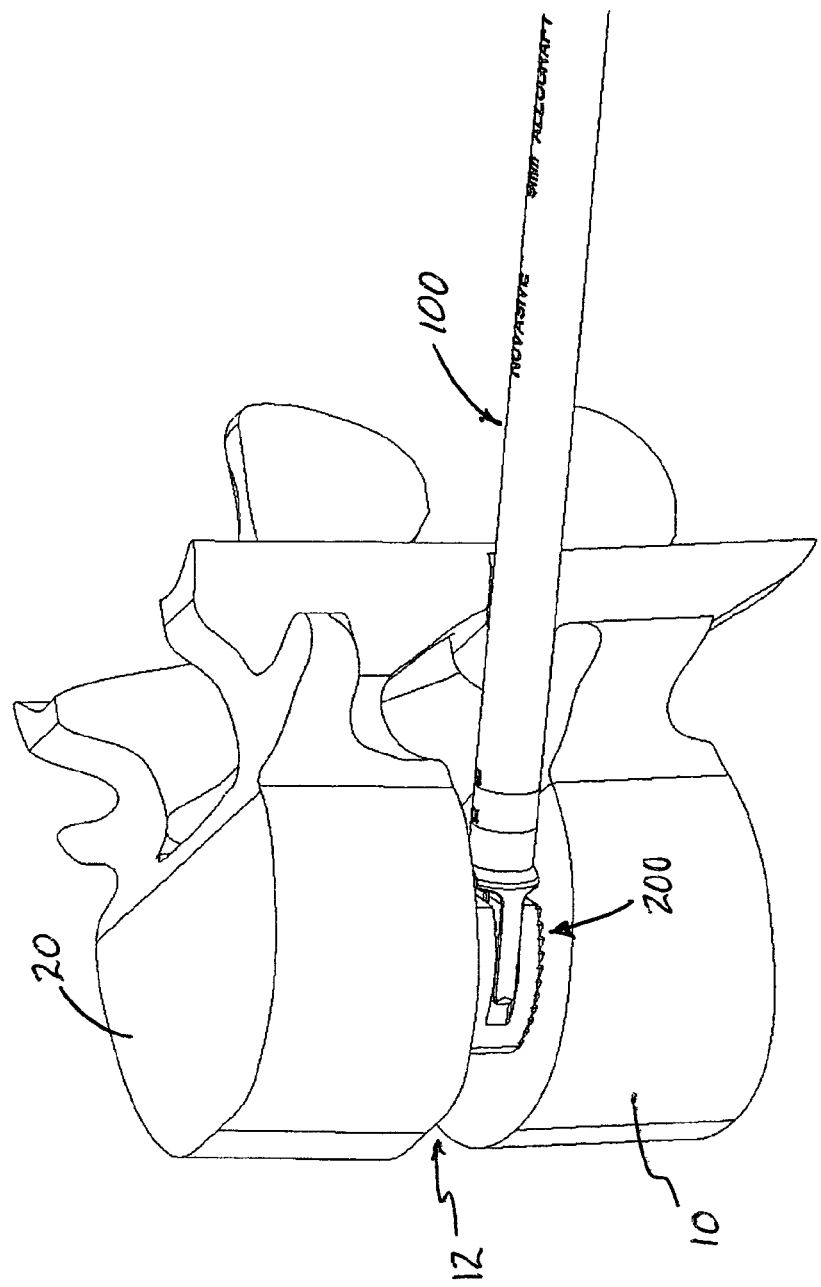
FIG. 5 is a sectional view of an exemplary 9 mm implant coupled to an exemplary 9 mm inserter positioned between vertebrae in accordance with the present invention.
Figure 6:
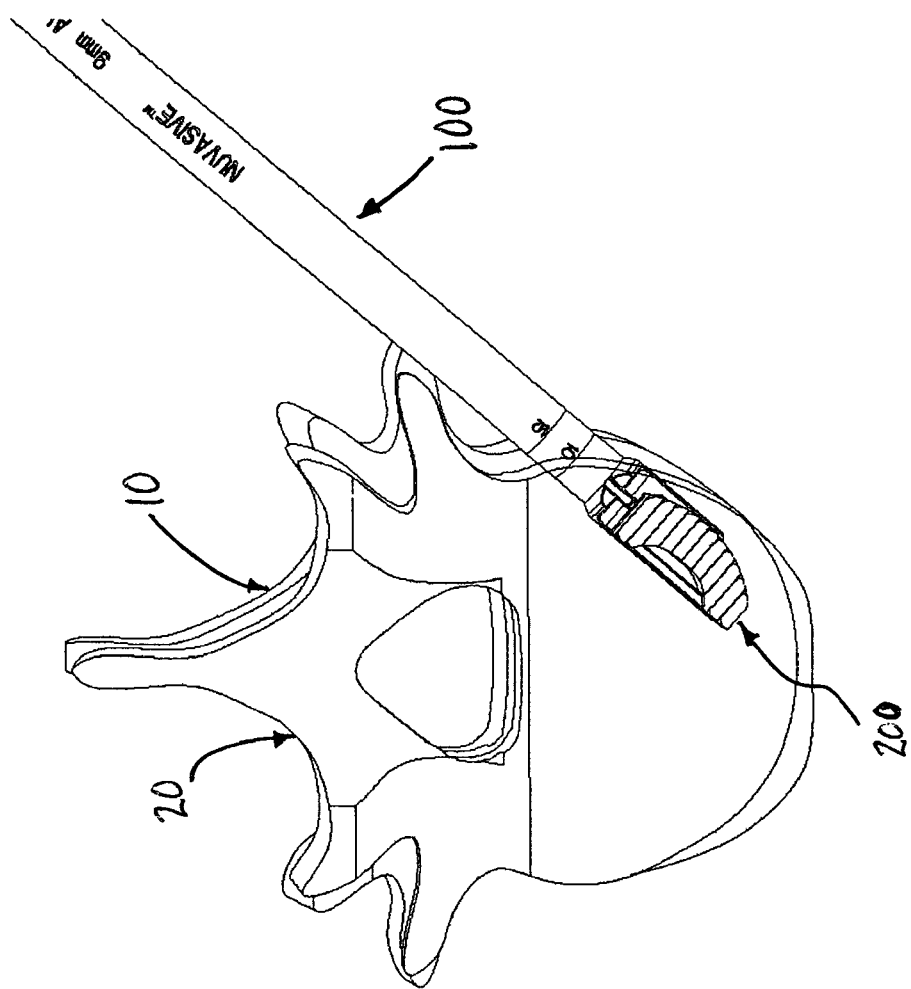
FIG. 6 is a top-sectional view of an exemplary 9 mm implant coupled to an exemplary 9 mm inserter positioned between vertebrae in accordance with the present invention.

FIGS. 1-4 depict a cut-away view of an exemplary process of inserting an exemplary implant 200 using an exemplary inserter 100 in accordance with the present invention. In this process an exemplary implant 200 (shown in sectional view) is inserted via an inserter 100 and cannula 300 into the disc space 12 of vertebrae 10 and 20. Upper vertebra 20 is shown in wire line view to more clearly show the advancement of the implant 200 and inserter 100 from FIG. 1 to FIG. 4 into the disc space 12. As shown in these figures, the inserter 100 grips the implant 200 via a set of prongs (described below). Ideally the prongs are fluoroscopically opaque. Accordingly, as the implant 200 is advanced from a position outside the disc space (as shown in FIG. 1) to a desired position (as shown in FIG. 4), fluoroscopic images of the vertebrae 10 and 20 would enable a clinician to determine the implant location in the disc space 12 by observing the inserter's prongs position. Accordingly, the inserter 100 and method of the present invention may be used to accurately place an implant 200 within a disc space 12 regardless of the fluoroscopic properties of the implant 200 (fluoroscopically opaque or transparent). FIGS. 5-6 are different depictions or views of the exemplary implant 200 gripped by an exemplary inserter 100 between vertebrae 10 and 20 in accordance with the present invention.

FIGS. 7A to 10D are diagrams of dimensional variations of the exemplary implant 200. The exemplary implant 200 may have a width of 9 or 11 millimeters and a length of 20 or 25 millimeters. Further, as shown in Size Tables1-4, the exemplary implant 200 may have a height from 6 to 16 millimeters in 2 mm increments in one exemplary embodiment. The basic exemplary implant 200 geometry is similar for each of these size variations. As shown in FIGS. 7A to 10D, the implant 200 is crescent shaped with a top 210, bottom 220, proximal end 230, distal end 260, left side 240, and right side 250. The implant top 210 and bottom 220 include a plurality of rows of teeth 212 where the teeth are designed to engage vertebra endplates upon insertion between vertebrae. The implant sides 230, 240, 250, 260 include a plurality of tool engaging recesses 232, 234, 236, and 242. Implant's 200 left side 240 is curved while the tool recess 242 is straight. The implant's 200 right side has a curved section 252 and flat sections corresponding to the tool engaging recesses 234 and 236. The implants 200 proximal end 230 has a flat end and the tool engaging recess 232 also has a flat end with two 45-degree offset that mate with the tool recess 242 and 234.

Figures 7A, 7B:
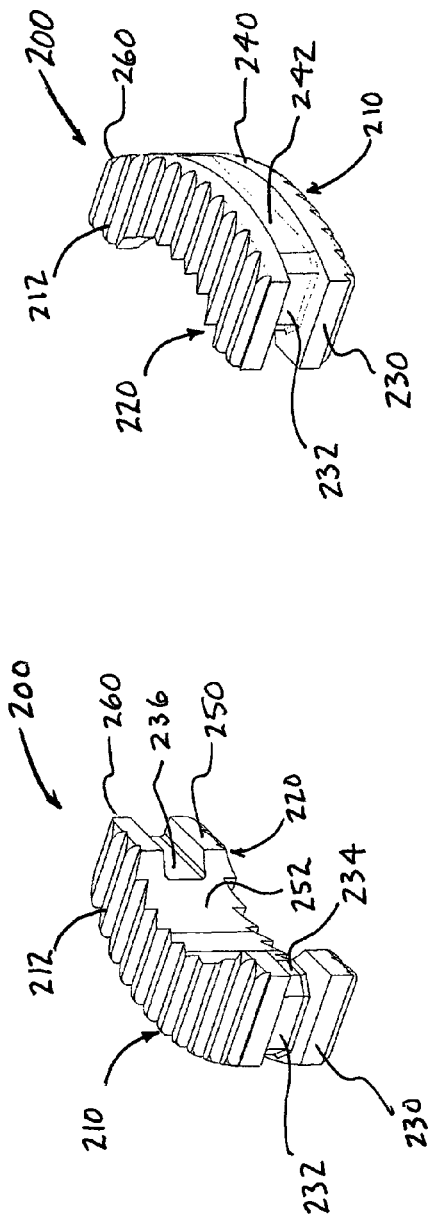
FIG. 7A is a right side isometric view of an 8 mm tall, 9 mm wide, 20 mm long bony implant in accordance with the present invention.
FIG. 7B is a left side isometric view of the 8 mm tall, 9 mm wide, 20 mm long bony implant in accordance with the present invention.
Figure 7C:
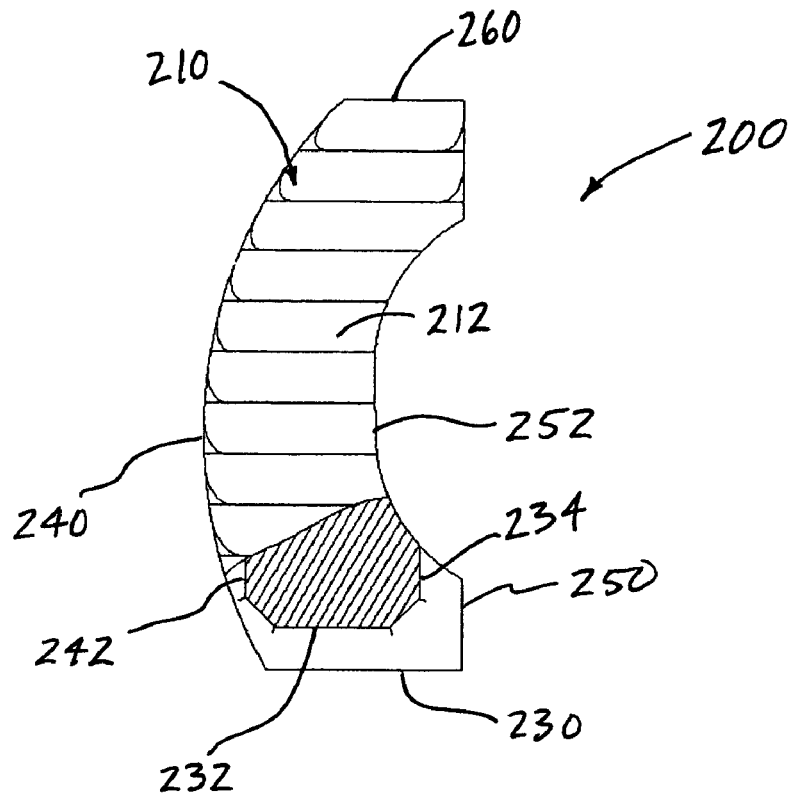
FIG. 7C is a top side view of the 8 mm tall, 9 mm wide, 20 mm long bony implant in accordance with the present invention.
Figure 7D:
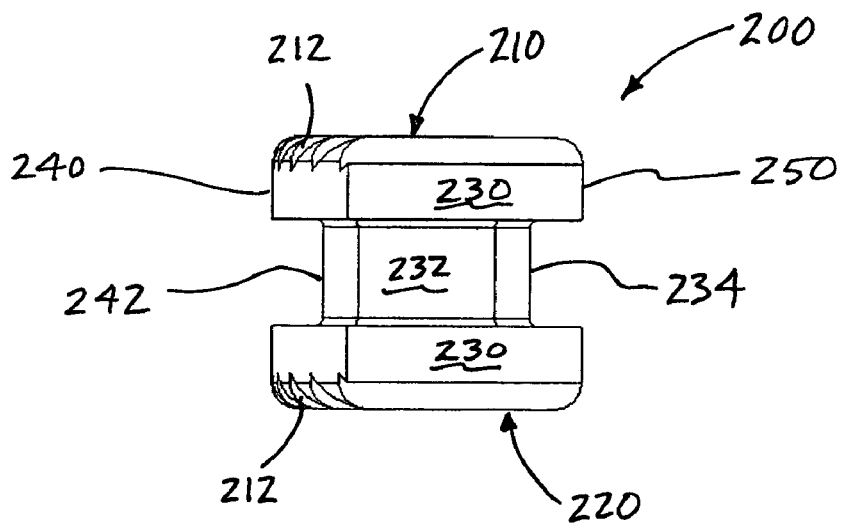
FIG. 7D is a tool base engaging side view of the 8 mm tall, 9 mm wide, 20 mm long bony implant in accordance with the present invention.
Figure 7E:
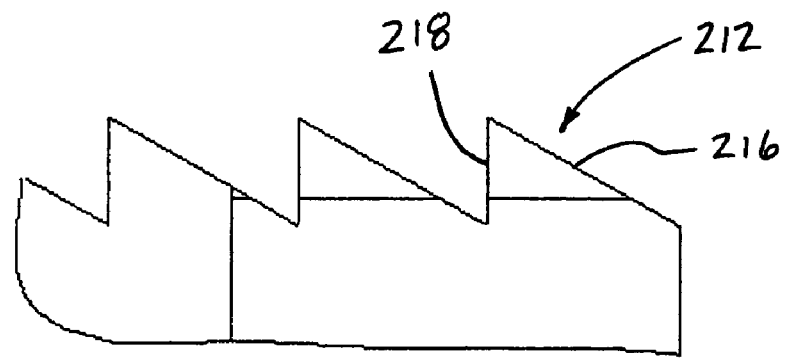
FIG. 7E is an exploded view of a 20 mm long bony implant's teeth in accordance with the present invention.
Figure 7F:
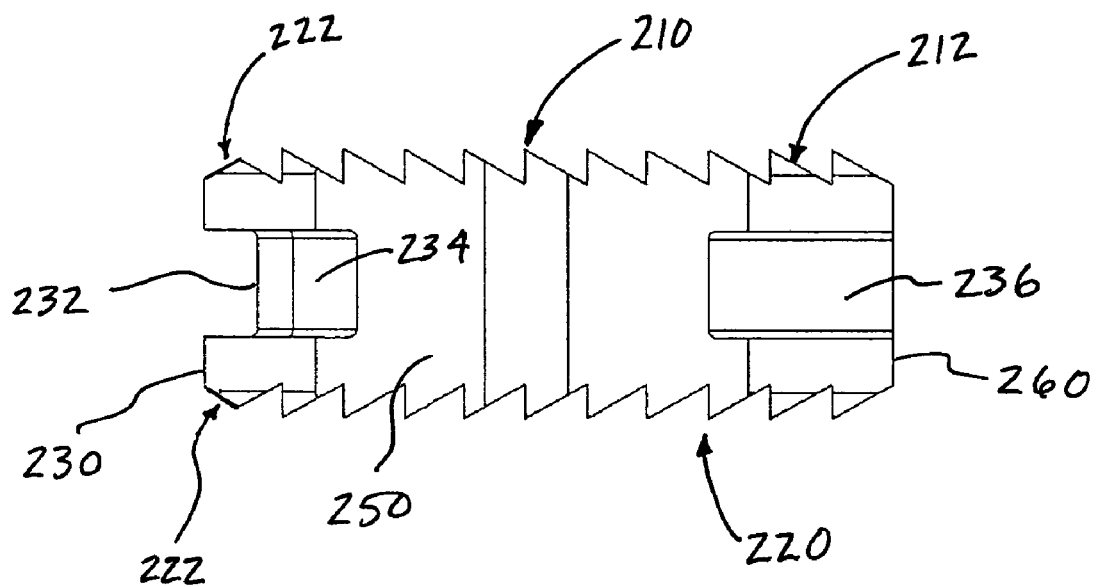
FIG. 7F is a view of the tool long side engaging side of an 8 mm tall, 20 mm long bony implant in accordance with the present invention.

In further detail, FIG. 7A is a top, right side isometric line drawing of an exemplary 8 mm tall, 9 mm wide, 20 mm long implant 200. FIG. 7B is a bottom, left side isometric line drawing of the exemplary 8 mm tall, 9 mm wide, 20 mm long implant 200. FIG. 7C is a top view line drawing of the exemplary 8 mm tall, 9 mm wide, 20 mm long implant 200. FIG. 7D is a proximal end view line drawing of the exemplary 8 mm tall, 9 mm wide, 20 mm long implant 200. FIG. 7F is a right side view line drawing of an exemplary 8 mm tall, 20 mm long implant 200 illustrating the general shape of two 45-degree teeth 222 disposed on the proximal end 230. FIG. 7E is a detailed view line drawing of several teeth 212 for an exemplary 8 mm tall, 20 mm long implant 200. As shown, each tooth has a top 216 and side 218 where the top has an inclination of 60-degree relative to the flat surface of the implant top 210 or bottom 220. As indicated, the exemplary 20 mm long implant 200 has 22 such teeth 212.

Figures 8A, 8B:
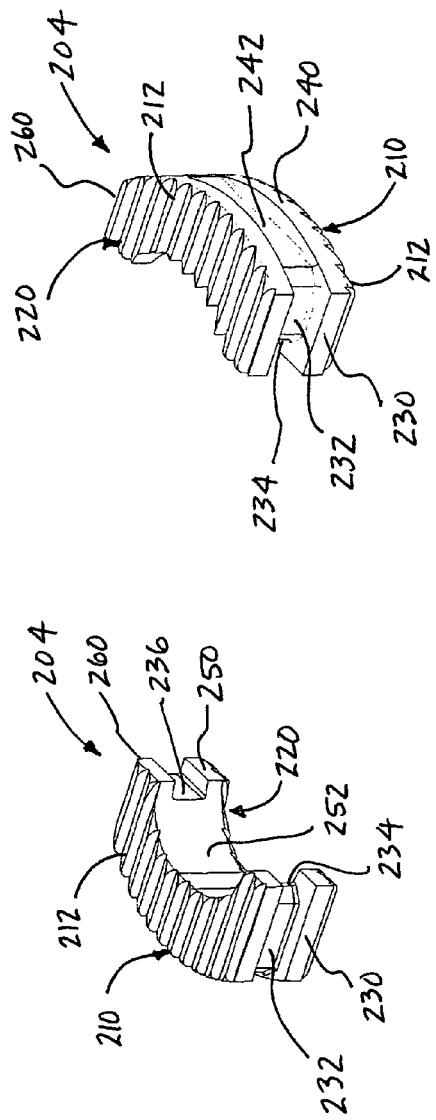
FIG. 8A is a right side isometric view of an 8 mm tall, 11 mm wide, 20 mm long bony implant in accordance with the present invention.
FIG. 8B is a left side view of the 8 mm tall, 11 mm wide, 20 mm long bony implant in accordance with the present invention.
Figure 8C:
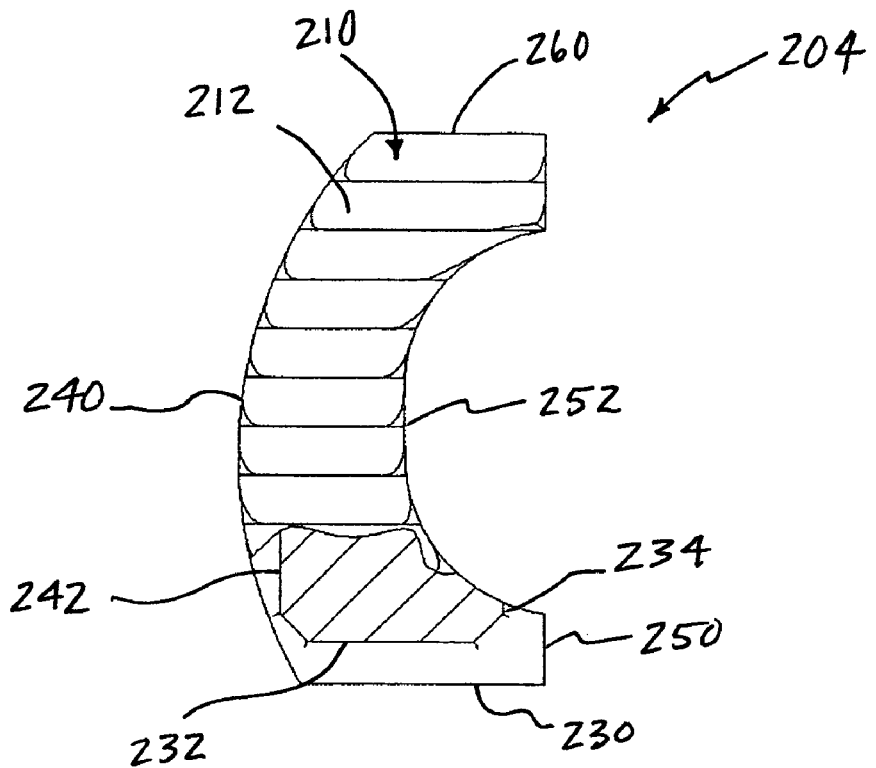
FIG. 8C is a top side view of the 8 mm tall, 11 mm wide, 20 mm long bony implant in accordance with the present invention.
Figure 8D:
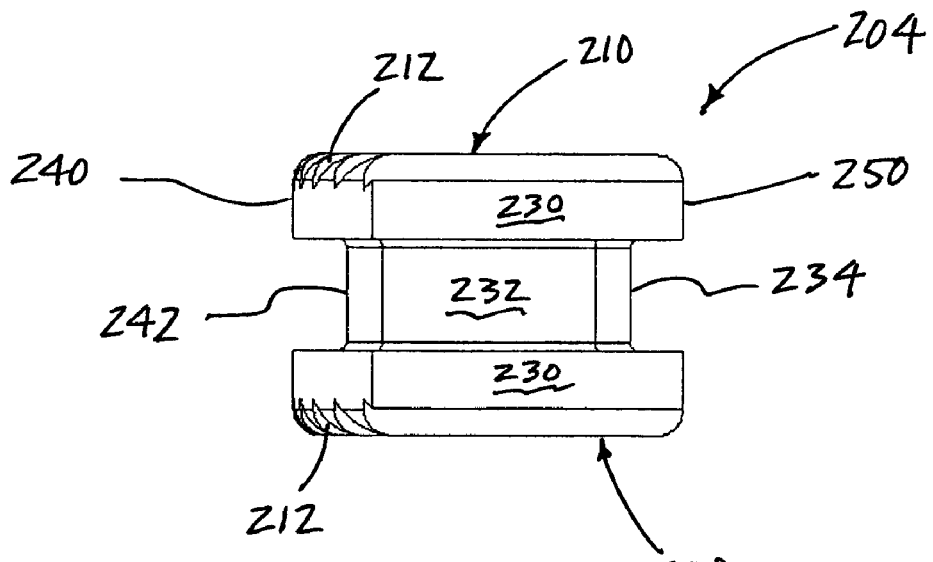
FIG. 8D is a tool base engaging side view of the 8 mm tall, 11 mm wide, 20 mm long bony implant in accordance with the present invention.

FIG. 8A is a top, right side isometric line drawing of an exemplary 8 mm tall, 11 mm wide, 20 mm long implant 204. FIG. 8B is a bottom, left side isometric line drawing of the exemplary 8 mm tall, 11 mm wide, 20 mm long implant 204. FIG. 8C is a top view line drawing of the exemplary 8 mm tall, 11 mm wide, 20 mm long implant 204. FIG. 8D is a proximal end view line drawing of the exemplary 8 mm tall, 11 mm wide, 20 mm long implant 204.

Figures 9A, 9B:
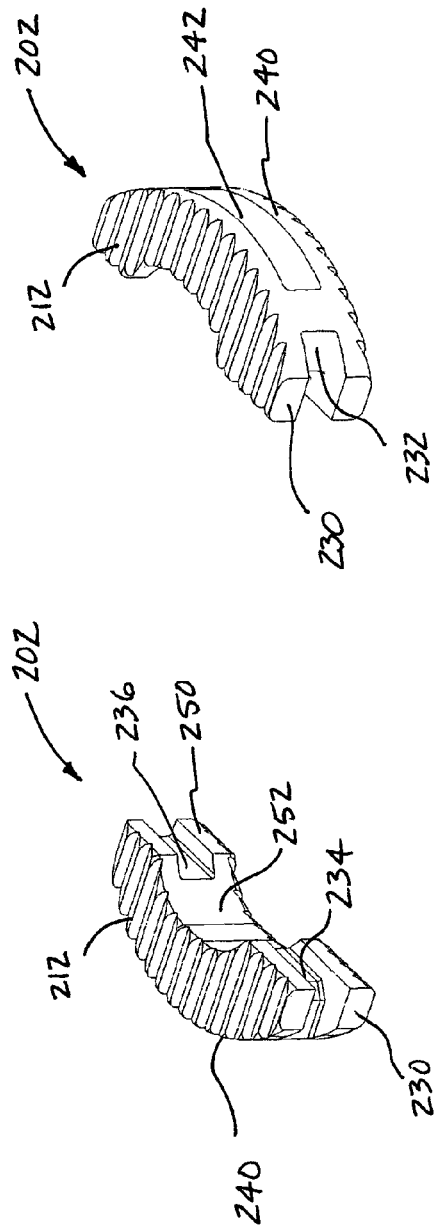
FIG. 9A is a right side isometric view of an 8 mm tall, 9 mm wide, 25 mm long bony implant in accordance with the present invention.
FIG. 9B is a left side isometric view of the 8 mm tall, 9 mm wide, 25 mm long bony implant implant in accordance with the present invention.
Figure 9C:
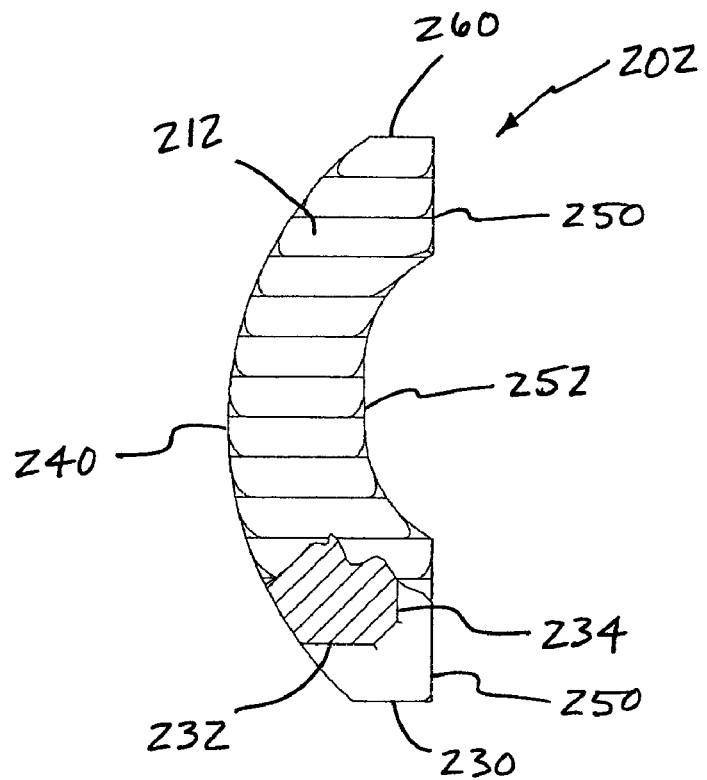
FIG. 9C is a top side view of the 8 mm tall, 9 mm wide, 25 mm long bony implant in accordance with the present invention
Figure 9D:
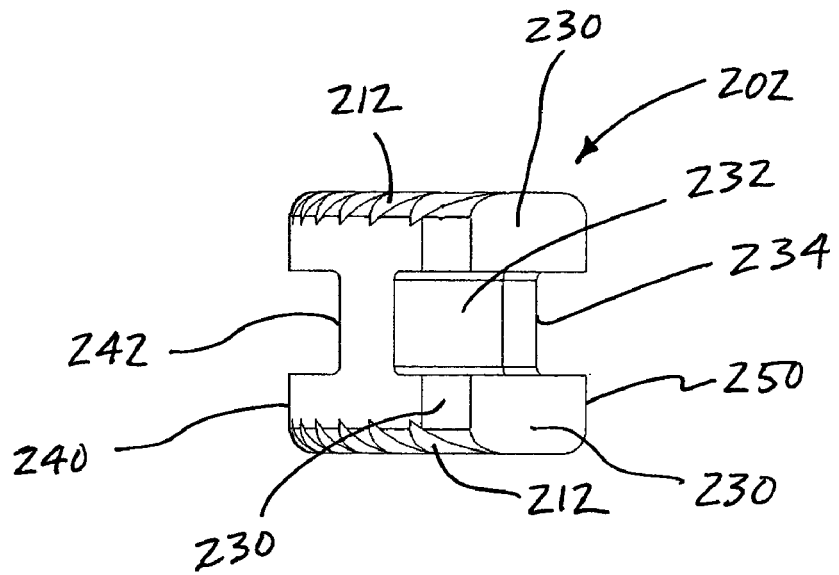
FIG. 9D is a tool base engaging side view of the 8 mm tall, 9 mm wide, 25 mm long bony implant implant in accordance with the present invention
Figure 9E:
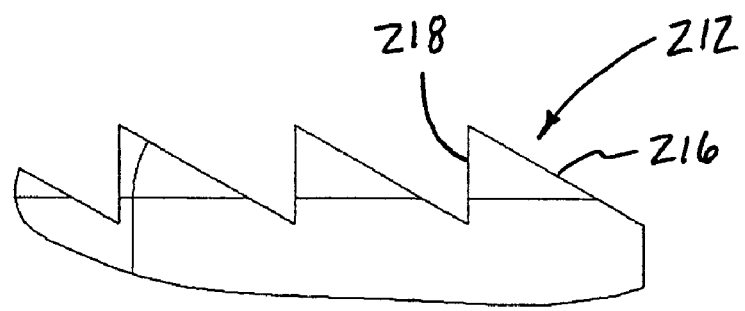
FIG. 9E is an exploded view of a 25 mm long bony implant implant's teeth in accordance with the present invention
Figure 9F:
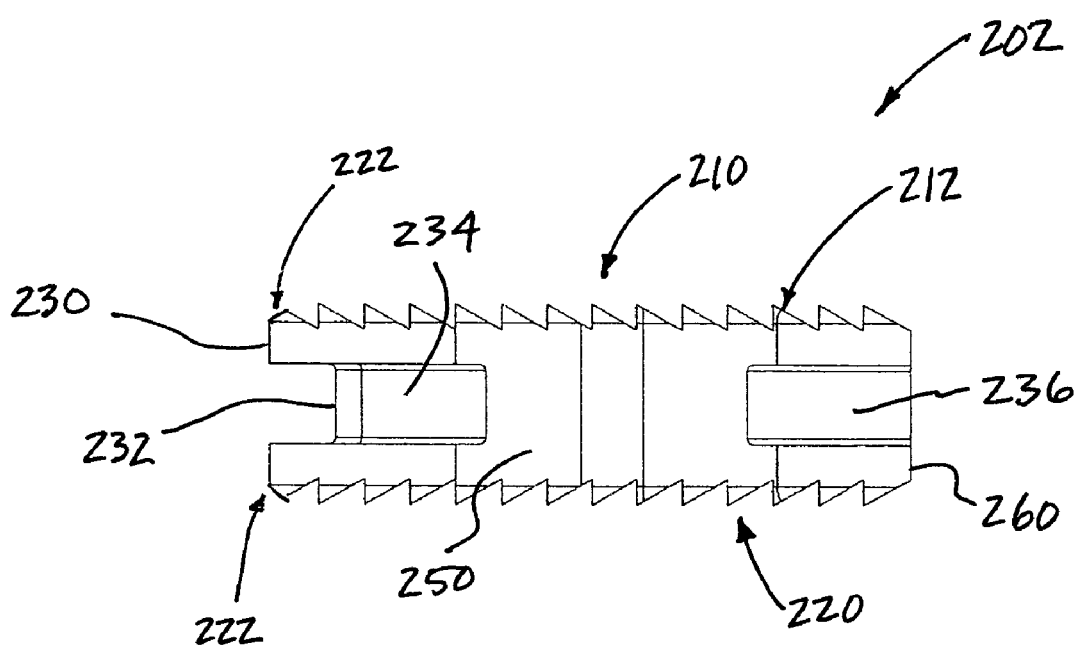
FIG. 9F is a view of the tool long side engaging side of an 8 mm tall, 25 mm long bony implant in accordance with the present invention

In further detail, FIG. 9A is a top, right side isometric line drawing of an exemplary 8 mm tall, 9 mm wide, 25 mm long implant 202. FIG. 9B is a bottom, left side isometric line drawing of the exemplary 8 mm tall, 9 mm wide, 25 mm long implant 202. FIG. 9C is a top view line drawing of the exemplary 8 mm tall, 9 mm wide, 25 mm long implant 202. FIG. 9D is a proximal end view line drawing of the exemplary 8 mm tall, 9 mm wide, 25 mm long implant 202. FIG. 9F is a right side view line drawing of an exemplary 8 mm tall, 25 mm long implant 202 that indicates the dimensions of the two 45-degree teeth 222. FIG. 9E is a detailed view line drawing of several teeth 212 for an exemplary 25 mm long implant 202. As shown, each tooth has a top 216 and side 218 where the top has an inclination of 60-degree relative to the flat surface of the implant top 210 or bottom 220. As indicated, the exemplary 25 mm long implant 200 has 28 such teeth 212.

Figure 10B:
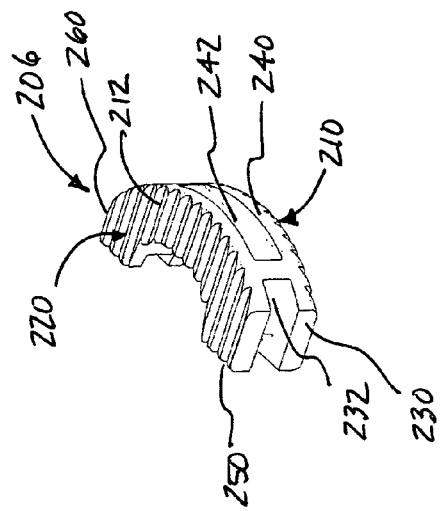
FIG. 10B is a left side isometric view of the 8 mm tall, 11 mm wide, 25 mm long bony implant in accordance with the present invention
Figure 10A:
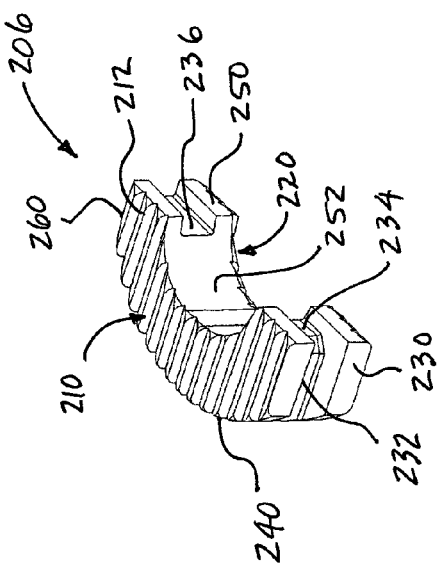
FIG. 10A is a right side isometric view of an 8 mm tall, 11 mm wide, 25 mm long bony implant in accordance with the present invention
Figure 10C:
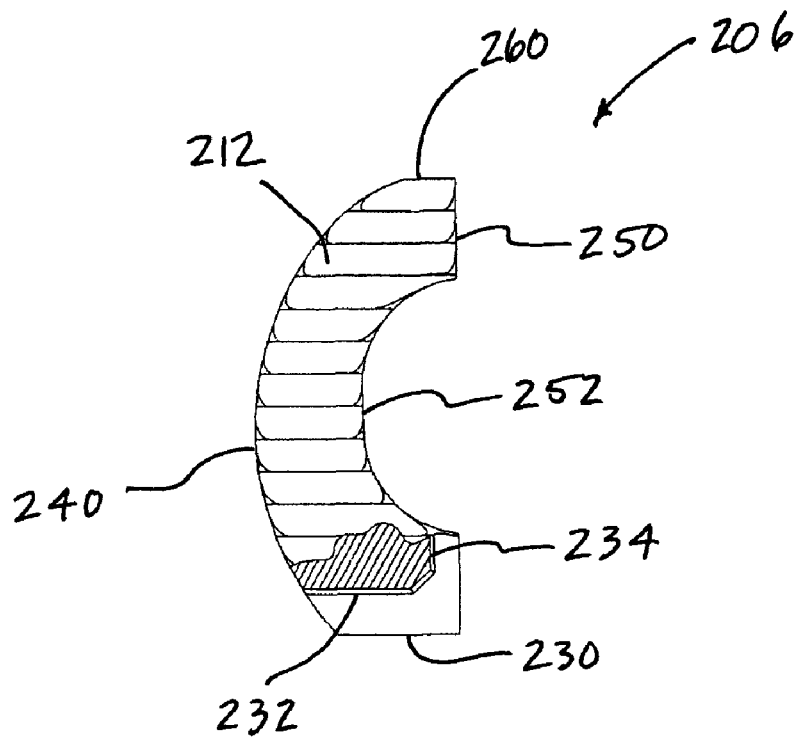
FIG. 10C is a top side isometric view of the 8 mm tall, 11 mm wide, 25 mm long bony implant in accordance with the present invention
Figure 10D:
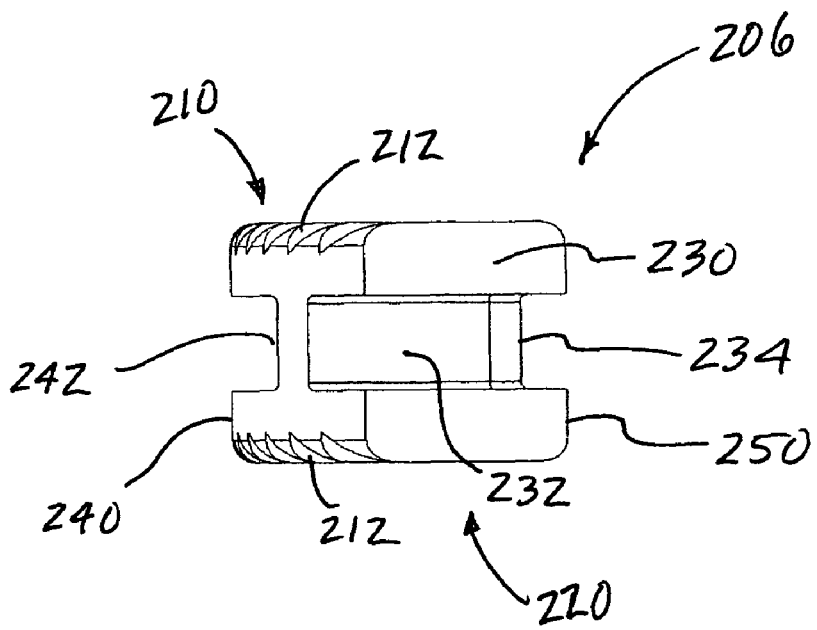
FIG. 10D is a tool base engaging side view of the 8 mm tall, 11 mm wide, 25 mm long bony implant in accordance with the present invention

FIG. 10A is a top, right side isometric line drawing of an exemplary 8 mm tall, 11 mm wide, 25 mm long implant 206. FIG. 10B is a bottom, left side isometric line drawing of the exemplary 8 mm tall, 11 mm wide, 25 mm long implant 206. FIG. 10C is a top view line drawing of the exemplary 8 mm tall, 11 mm wide, 25 mm long implant 206. FIG. 10D is a proximal end view line drawing of the exemplary 8 mm tall, 11 mm wide, 25 mm long implant 206.

FIGS. 11 to 25 are diagrams of views of different configurations of the exemplary inserter 100 in accordance with the invention. FIG. 11 is an isometric line drawing of the 9 mm wide implant inserter 100 in its two parts: the collar 110 and fork 120. The fork includes a shaft 122, proximal tool engaging end 126 and distal implant gripping end 124. The fork's 120 proximal end 126 includes a set of external threads 115. The collar 110 includes a hollow sleeve 112 dimensioned to slide over the proximal end 126 of the fork and engage the distal end 124. The collar 110 includes a grip 114 with internal receiving threads 128 therein where the internal receiving threads 128 engage the fork's external threads 115 when the sleeve 112 is slid over the fork's proximal end 126 and approaches the fork's distal end 124. The grip 114 is rotated clockwise to further advance the collar's 110 distal end. The fork's distal end 124 is dimensioned so that the collar 110 will compress the set of prongs upon advancement of the collar's 110 distal end by clockwise rotation of the sleeve 112 via the grip 114. When an implant 200 is placed between the set of prongs, the prongs may be advanced toward each other to securely engage the implant 200 upon clockwise rotation of the grip 114. The implant 200 may be similarly released from the set of prongs by rotating the sleeve 112 counterclockwise when desired, such as when the implant is positioned in a desired location between vertebrae 10 and 20 as shown in FIG. 4.

FIG. 12A is a top view of a line drawing of the 9 mm wide implant inserter 100 and FIG. 12B is a side view of the line drawing of the 9 mm wide implant inserter 100. As shown, the exemplary inserter 100 is about 10 inches in length from the distal end 124 to the grip 114. This enables a clinician to use the inserter 100 to place an implant 200 between vertebrae via a cannula 300 in a minimally invasive procedure. In such a procedure, an incision may be made on the patient's skin at location postero-lateral to the desired implant location. Then a trocar or other instrument may be advanced to the annulus of the disc between the vertebrae 10 and 20 of interest. A cannula may then be advanced over the trocar to engage the disc annulus. A clinician may perform an annulotomy to remove a section of the annulus and a discectomy thereafter to remove a portion of the disc where the implant 200 is to be placed. Further, the clinician may partially decorticate the endplates of the vertebrae 10 and 20. At some point during this procedure, the clinician may distract the vertebrae 10 and 20 to expand the disc space to a desired height. Based on the distraction height and the size of the vertebrae 10 and 20, the clinician may select a suitably dimensioned implant 200. The implant is then placed between the prongs of the inserter's distal end 124 and the prongs compressed by rotating the sleeve 112 via grip 114 to securely engage the implant 200.

Then, the clinician may insert the implant 200 into the disc space 12 via the inserter 100 and cannula 300. As noted, the clinician may take several fluoroscopic pictures to determine the location of the implant 200 within the disc space 12 by observing the location of the inserter's distal end 124, in particular the set of prongs. Upon placement of the implant 200 in the desired location within the disc space, the clinician may release the implant 200 by rotating the sleeve 112 via the grip 114 counter-clockwise to decompress the set of prongs 132 and 134. The clinician may remove any distraction means prior to the removal of the inserter so the vertebral endplates of the vertebrae 10 and 20 engage with the teeth 112 of the implant's 200 top 210 and bottom 220. Thereafter, the inserter 100 may be withdrawn, the annulotomy closed, the cannula removed, and the incision closed.

Figure 13C:
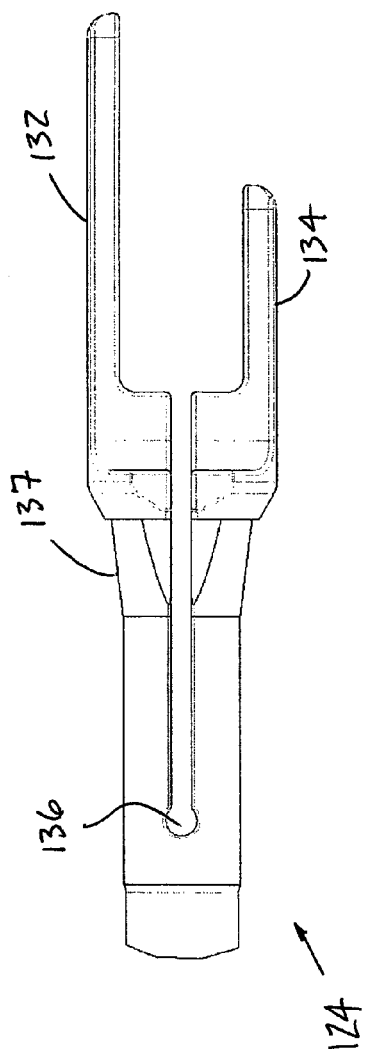
FIG. 13C is a detailed top view diagram of the exemplary 9 mm wide implant insertion tool fork distal end in accordance with the present invention.
Figure 13D:
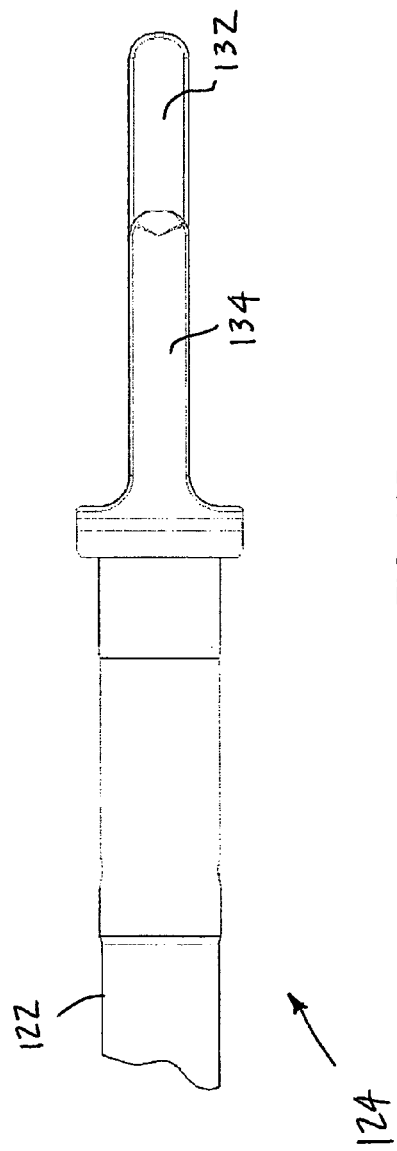
FIG. 13D is a detailed side view diagram of the exemplary 9 mm wide implant insertion tool fork distal end in accordance with the present invention.
Figure 13E:
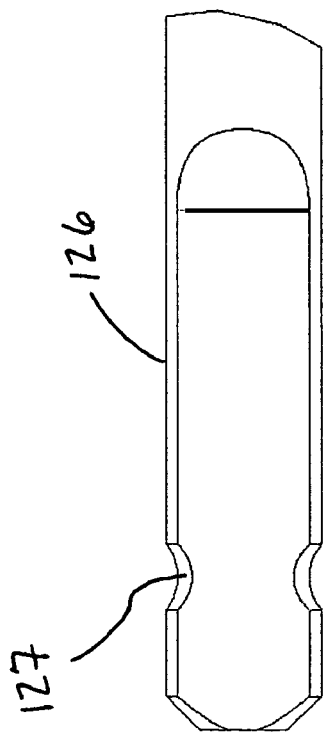
FIG. 13E is a detailed side view diagram of the exemplary 9 mm wide implant insertion tool fork proximal end in accordance with the present invention.
Figure 13F:
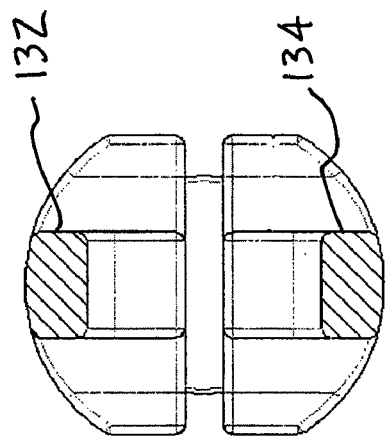
FIG. 13F is a detailed end view diagram of the exemplary 9 mm wide implant insertion tool fork distal end in accordance with the present invention.

FIGS. 13A to 13F are line drawings of the exemplary 9 mm wide implant fork 120 FIG. 13A is a side view line drawing of the fork 120 that, in one embodiment, has an overall length of about 12.40 inches and the distal end 124 length of about 1.035 inches. FIG. 13B is a top view line drawing of the fork 120 indicating additional exemplary dimensions. FIG. 13C is a top view line drawing of the fork's 120 distal end 124, FIG. 13D is a side view line drawing of the fork's 120 distal end 124, and FIG. 13F is an end view line drawing of the fork's 120 distal end 124. As shown, the distal end 124 includes a set of prongs 132 and 134 and a compressible section 136. As shown, the upper prong 132 may be compressed toward the lower prong 134 up to a distance of about 0.40 inches. In an exemplary embodiment, when the collar's 110 distal end is advanced over the tapered end 137 of the fork's 120 compressible section 136, the prongs 132 and 134 are compressed toward each other. FIG. 13E is a side view line drawing of the fork's 120 tool engaging proximal end 126. As shown, the tool engaging proximal end 126 includes a recess 127 to coupling to a handle (not shown).

FIGS. 14 to 16F are line drawings of an exemplary 11 mm wide implant inserter 100 in accordance with the present invention. FIG. 14 is an isometric line drawing of the 11 mm wide inserter in its two parts: the collar 110 and fork 120. FIG. 15A is a top view of a line drawing of the 11 mm wide implant inserter 100 and FIG. 15B is a side view of the line drawing of the 11 mm wide implant inserter 100. FIGS. 16A to 16F are line drawings of the exemplary 11 mm wide implant fork 120.

Figure 16A:
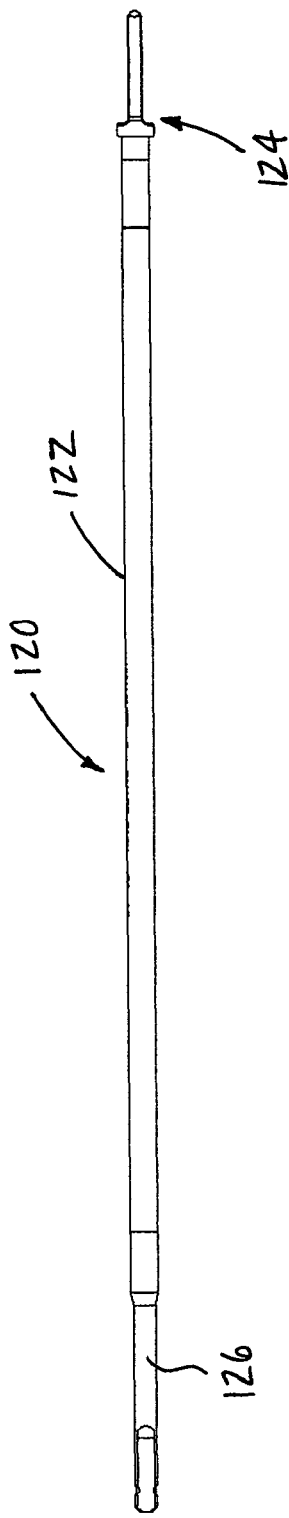
FIG. 16A is a side view diagram of the exemplary 11 mm wide implant insertion tool fork in accordance with the present invention.
Figure 16B:
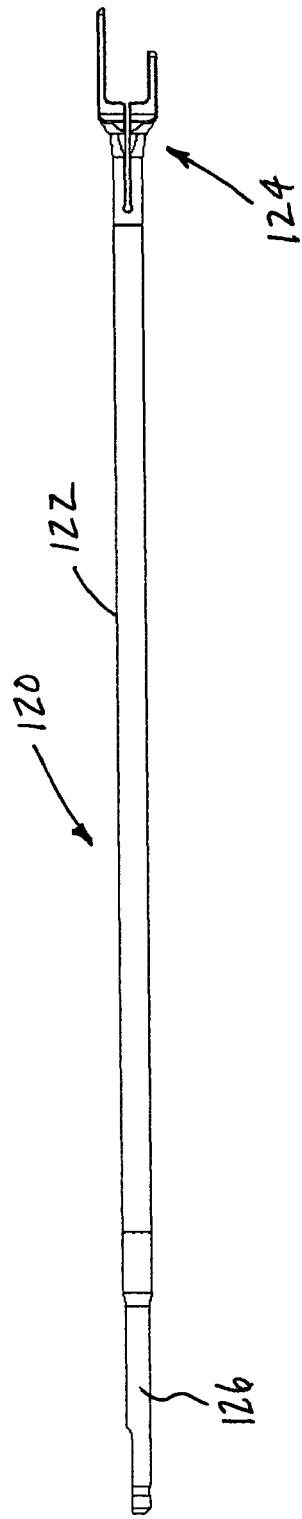
FIG. 16B is a top view diagram of the exemplary 11 mm wide implant insertion tool fork in accordance with the present invention.
Figure 16C:
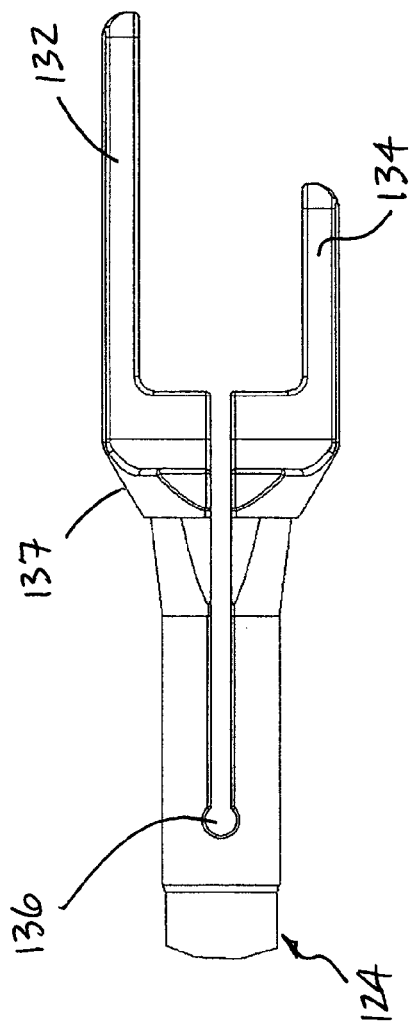
FIG. 16C is a detailed top view diagram of the exemplary 11 mm wide implant insertion tool fork distal end in accordance with the present invention.
Figure 16D:
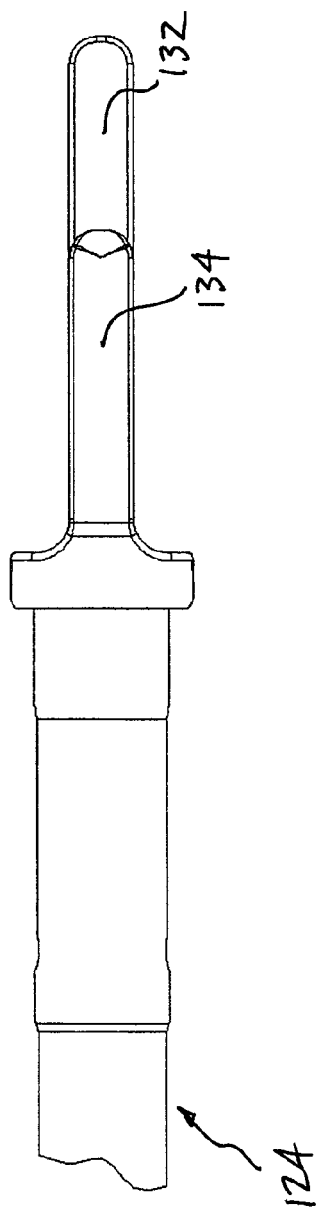
FIG. 16D is a detailed side view diagram of the exemplary 11 mm wide implant insertion tool fork distal end in accordance with the present invention.

FIG. 16A is a side view line drawing of the fork 120 that, in one embodiment, has an overall length of about 12.40 inches and a distal end 124 length of about 1.035 inches. FIG. 16B is a top view line drawings of the fork 120, FIG. 16C is a top view line drawing of the fork's 120 distal end 124, FIG. 16D is a side view line drawing of the fork's 120 distal end 124, and FIG. 16F is an end view line drawing of the fork's 120 distal end 124. FIG. 16E is a side view line drawing of the fork's 120 tool engaging proximal end 126.

Figure 17:
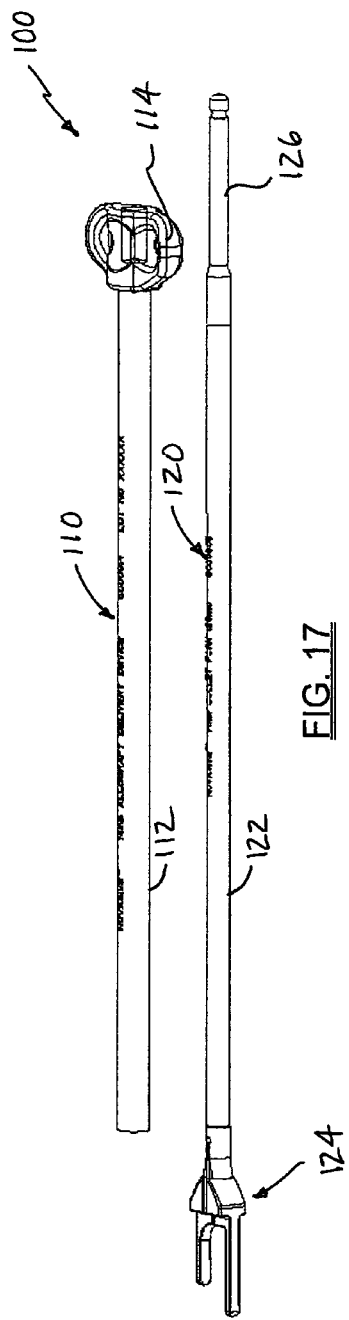
FIG. 17 is a diagram of an exemplary 14 mm wide implant insertion tool in two parts, an exemplary collar and fork in accordance with the present invention.
Figure 18A:
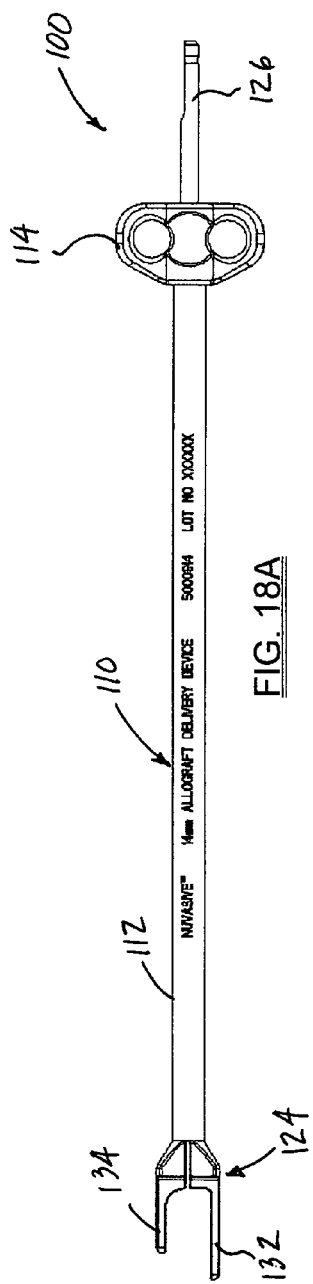
FIG. 18A is a top view diagram of the exemplary 14 mm wide implant insertion tool in accordance with the present invention.
Figure 18B:
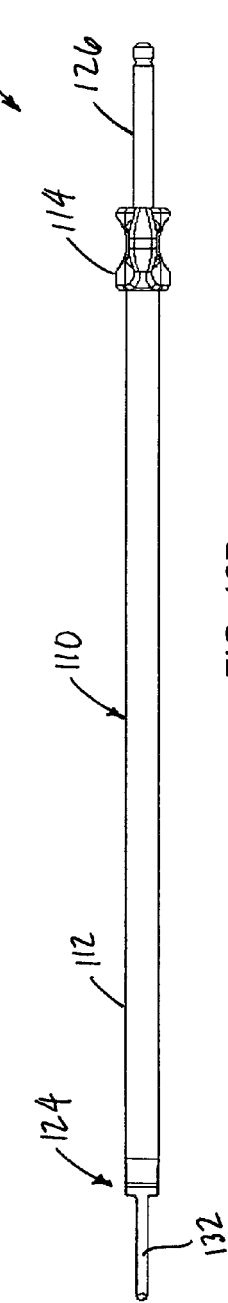
FIG. 18B is a side view diagram of the exemplary 14 mm wide implant insertion tool in accordance with the present invention.

The exemplary inserter 100 may be modified to handle implants having widths other than 9 and 11 mm. For example, FIGS. 17 to 18B are line drawings of an exemplary 14 mm wide implant inserter 100 in accordance with the present invention. FIG. 17 is an isometric line drawing of the 14 mm wide implant inserter 100 in its two parts: the collar 110 and fork 120. FIG. 18A is a top view of a line drawing of the 14 mm wide implant inserter 100 and FIG. 18B is a side view of the line drawing of the 14 mm wide implant inserter.

Figure 19:
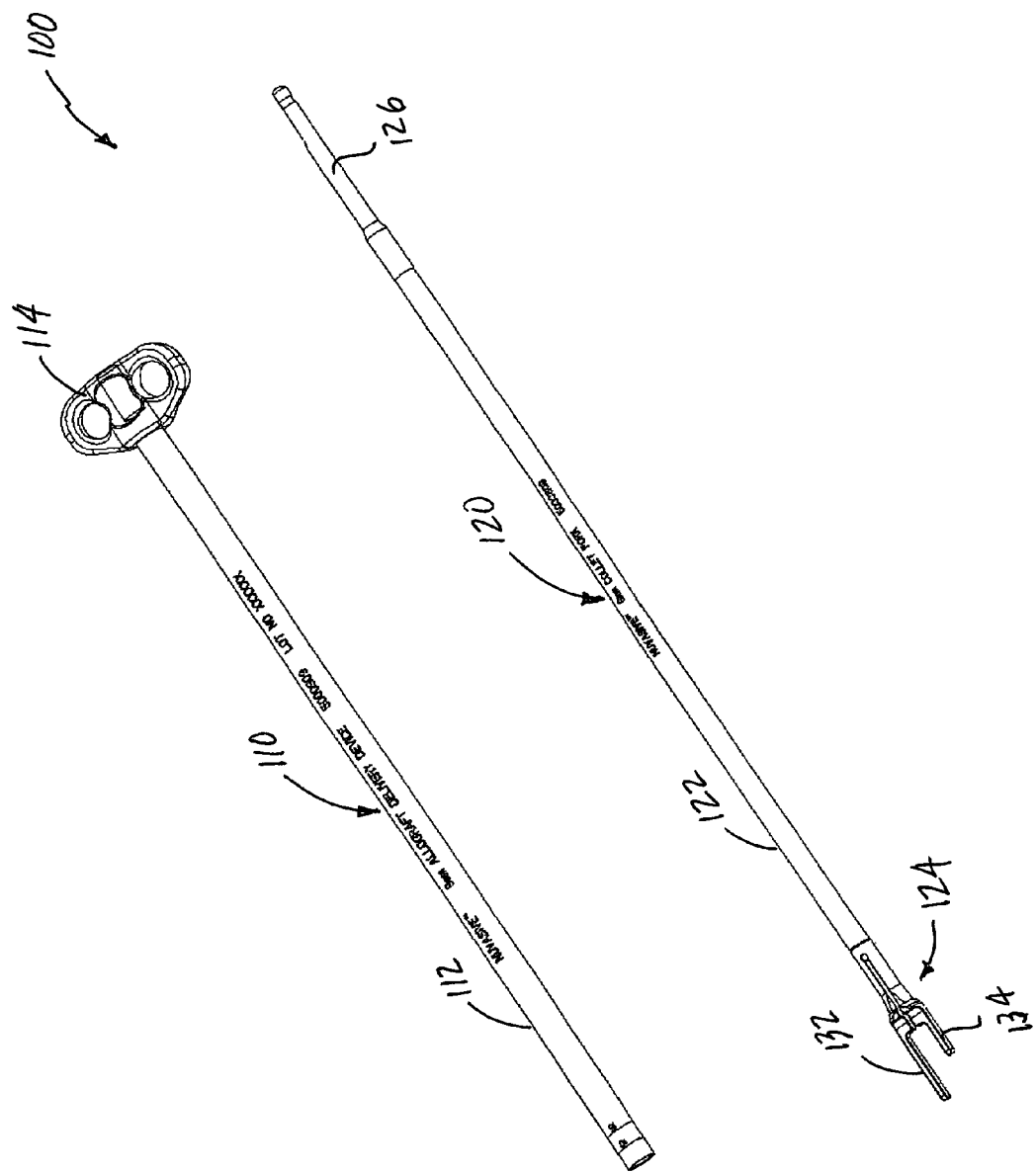
FIG. 19 is an isometric view of the exemplary 9 mm wide implant insertion tool in two parts, the exemplary collar and the fork in accordance with the present invention.
Figure 20:
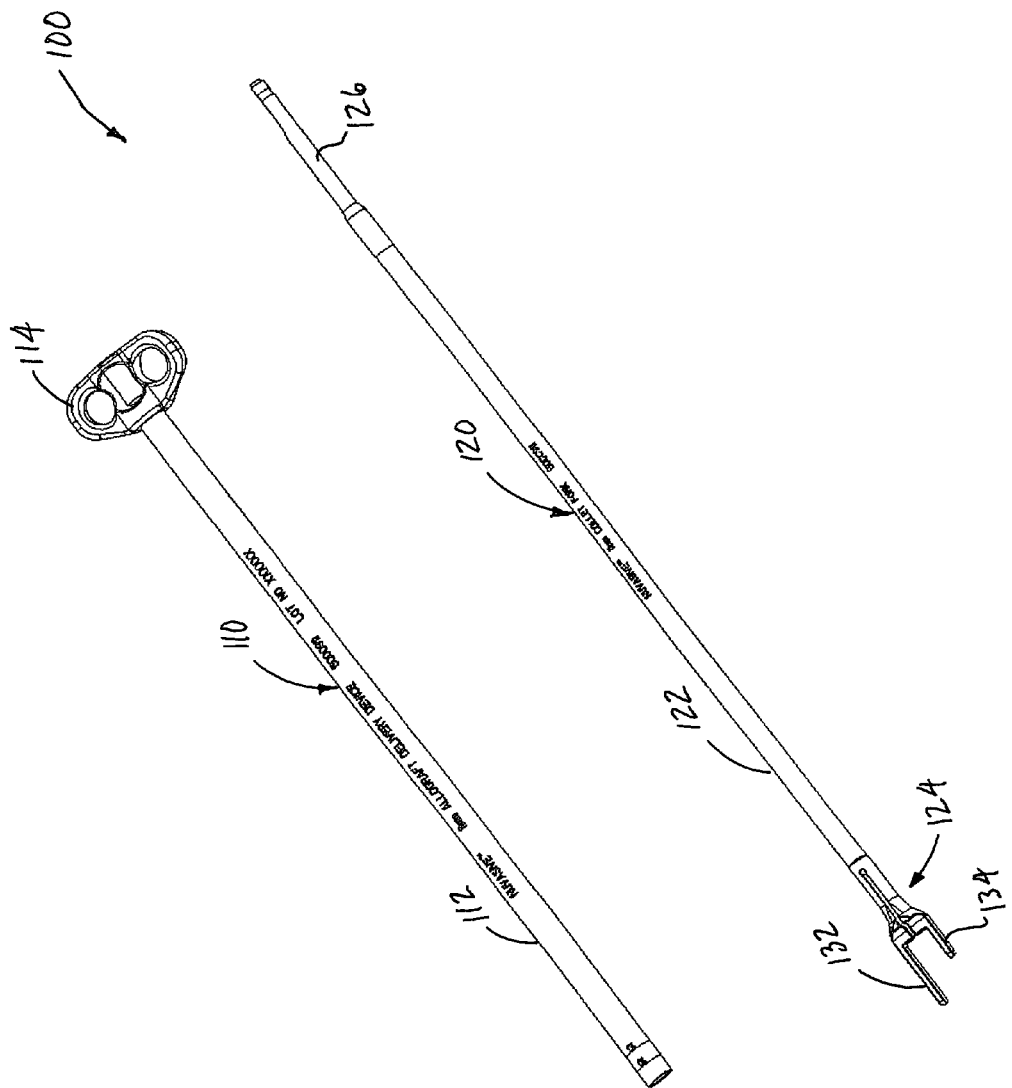
FIG. 20 is an isometric view of the exemplary 11 mm wide implant insertion tool in two parts, the exemplary collar and the fork in accordance with the present invention.
Figure 21A:
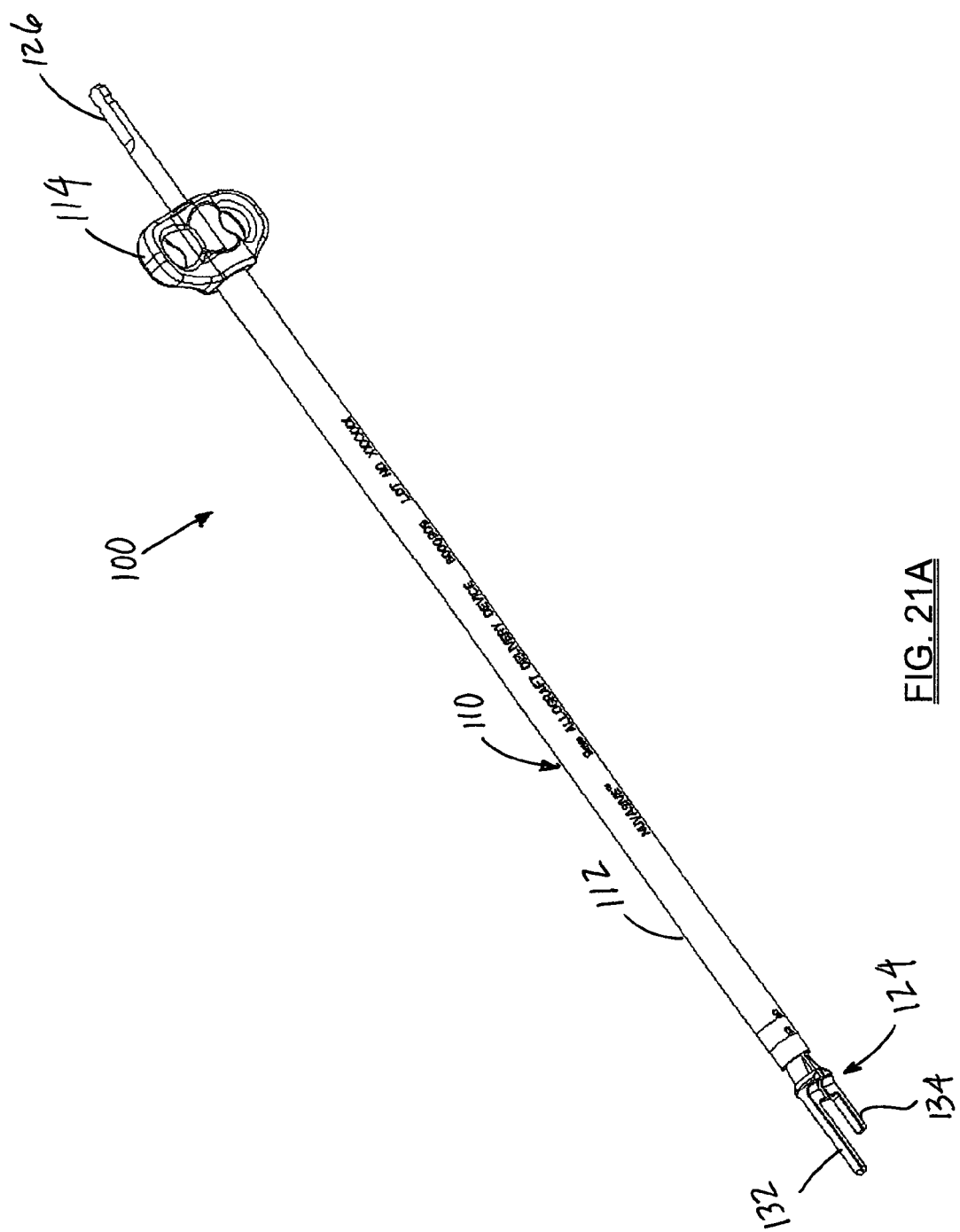
FIG. 21A is an isometric cross-sectional view of the exemplary 9 mm wide implant insertion tool in accordance with the present invention.
Figure 21C:
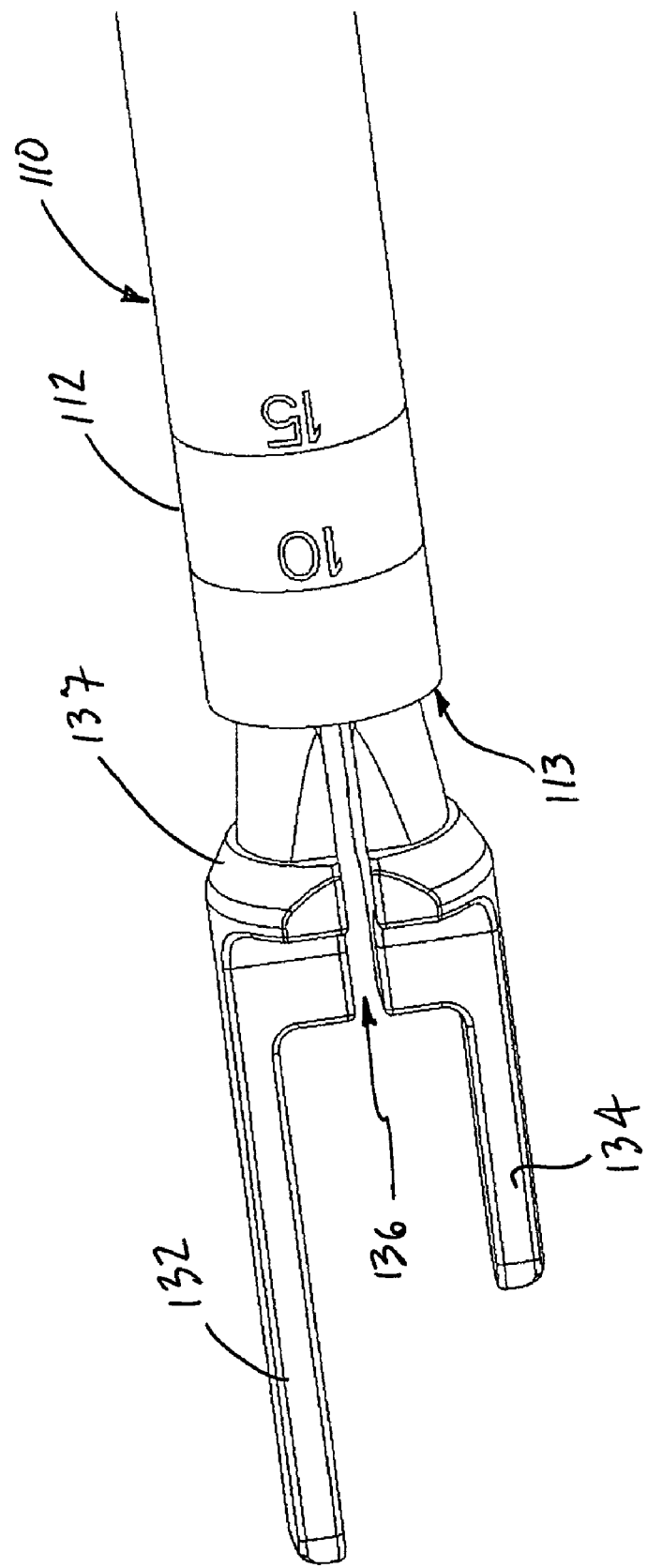
FIG. 21C is an isometric detailed cross-sectional view of the exemplary 9 mm wide implant insertion tool distal end in accordance with the present invention.
Figure 22:
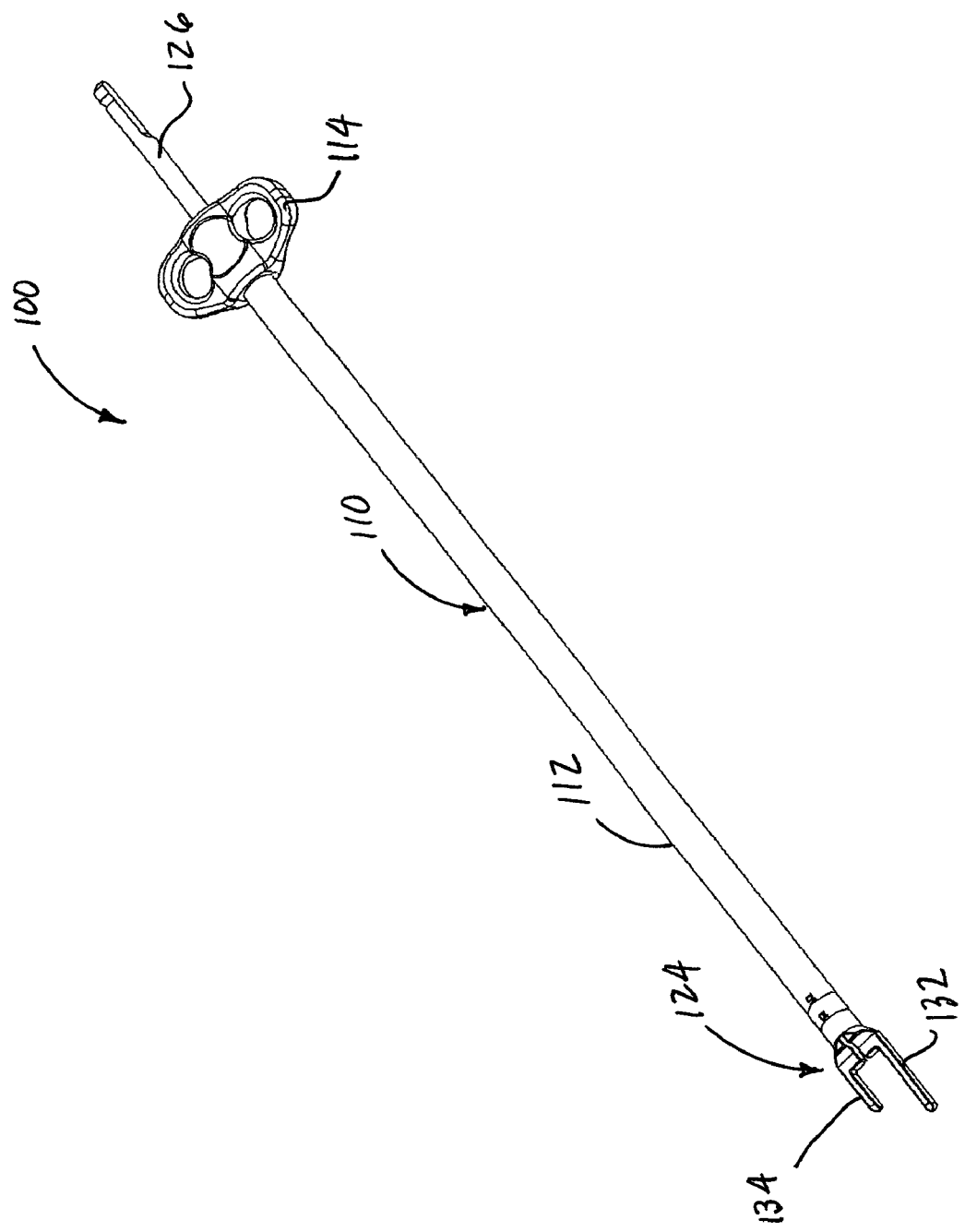
FIG. 22 is an isometric line diagram of the exemplary 11 mm wide implant insertion tool distal end in accordance with the present invention.
Figure 23:
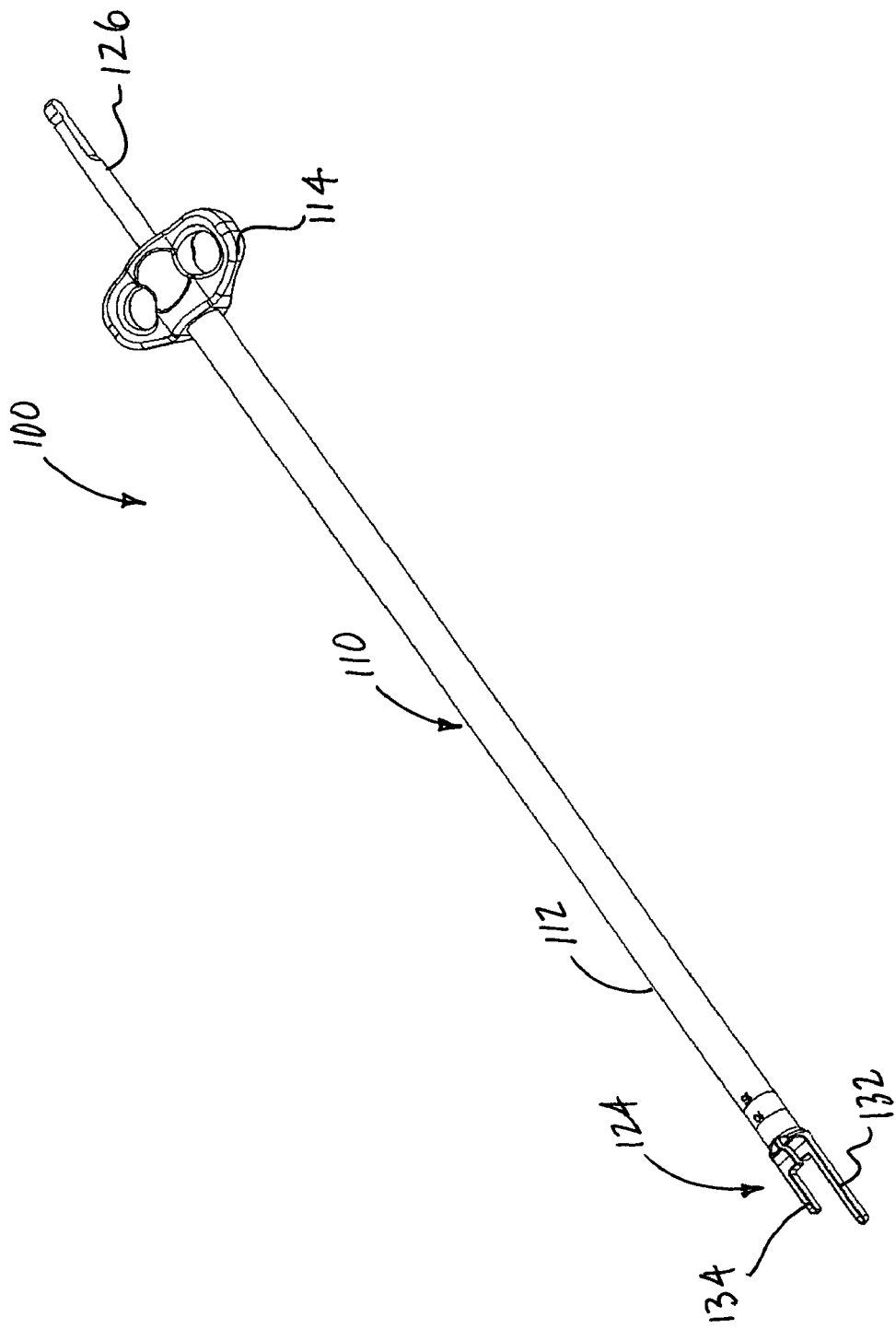
FIG. 23 is an isometric line diagram of the exemplary 9 mm wide implant insertion tool in accordance with the present invention.
Figure 24:
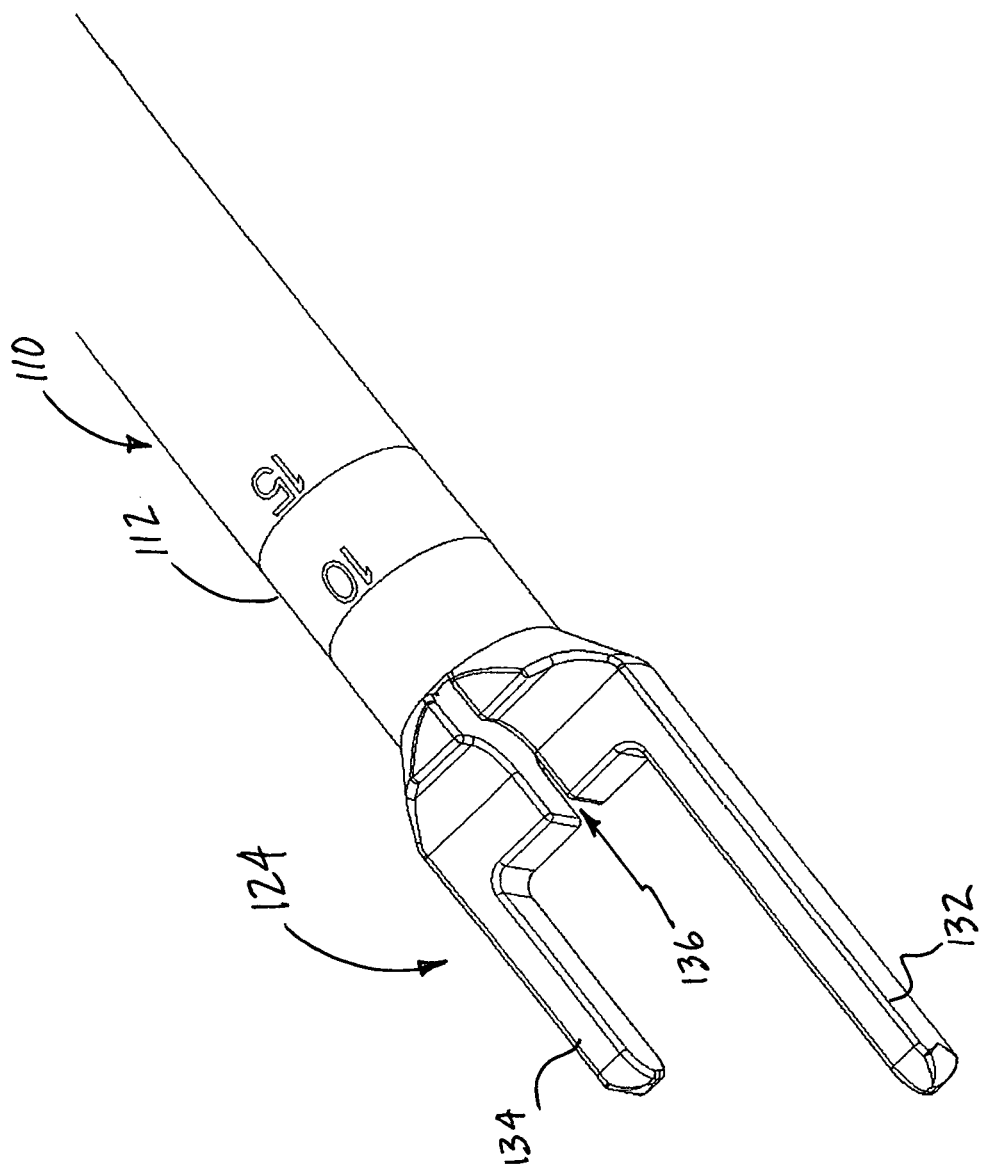
FIG. 24 is an isometric line diagram of the exemplary 11 mm wide implant insertion tool distal end in accordance with the present invention.
Figure 25:
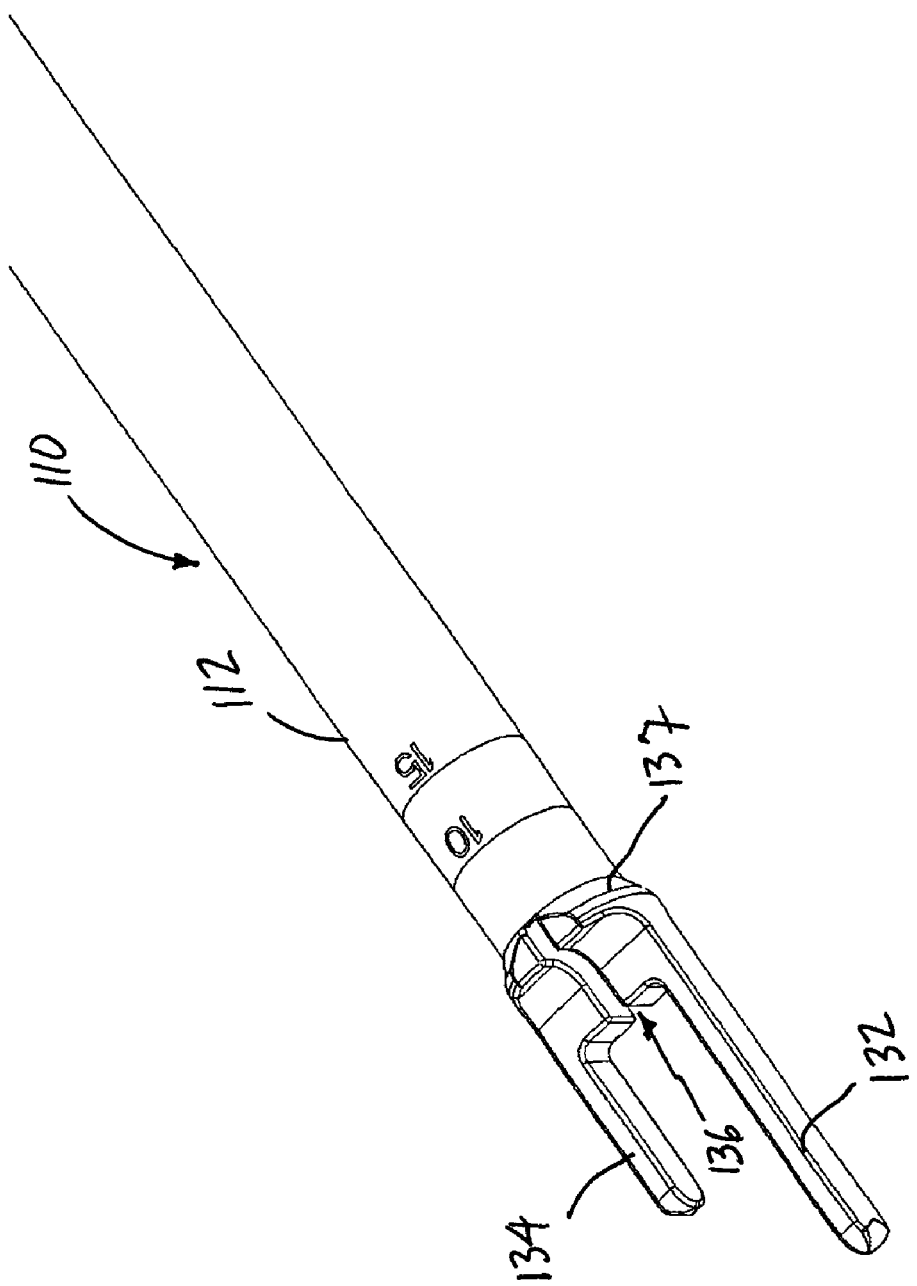
FIG. 25 is an isometric line diagram of the exemplary 9 mm wide implant insertion tool distal end in accordance with the present invention.

FIGS. 19 to 25 are additional views of the exemplary inserter 100 in accordance with the present invention. FIG. 19 is an isometric drawing of the 9 mm wide implant inserter 100 in its two parts: the collar 110 and fork 120. FIG. 20 is an isometric drawing of the 11 mm wide implant inserter 100 in its two parts: the collar 110 and fork 120. FIG. 21A is an isometric cross sectional drawing of the 9 mm wide implant inserter 100. FIG. 21B is an isometric cross sectional drawing of the 9 mm wide implant inserter 100 detailing its proximal end. In particular, FIG. 21B shows the engagement between the fork's external thread 128 and the collar's receiving thread 115. FIG. 21C is an isometric cross sectional drawing of the 9 mm wide implant inserter 100 detailing its distal end. In particular, FIG. 21C—shows the engagement between the fork's flared end 137 and the collar's sleeve tapered section 113. FIG. 22 is an isometric line drawing of the exemplary 11 mm wide implant inserter 100. FIG. 23 is an isometric line drawing of the exemplary 9 mm wide implant inserter 100. FIG. 24 is an isometric drawing (line) of the exemplary 11 mm wide implant inserter's distal end. FIG. 25 is an isometric drawing (line) of the exemplary 9 mm wide implant inserter's distal end.

Figure 26:
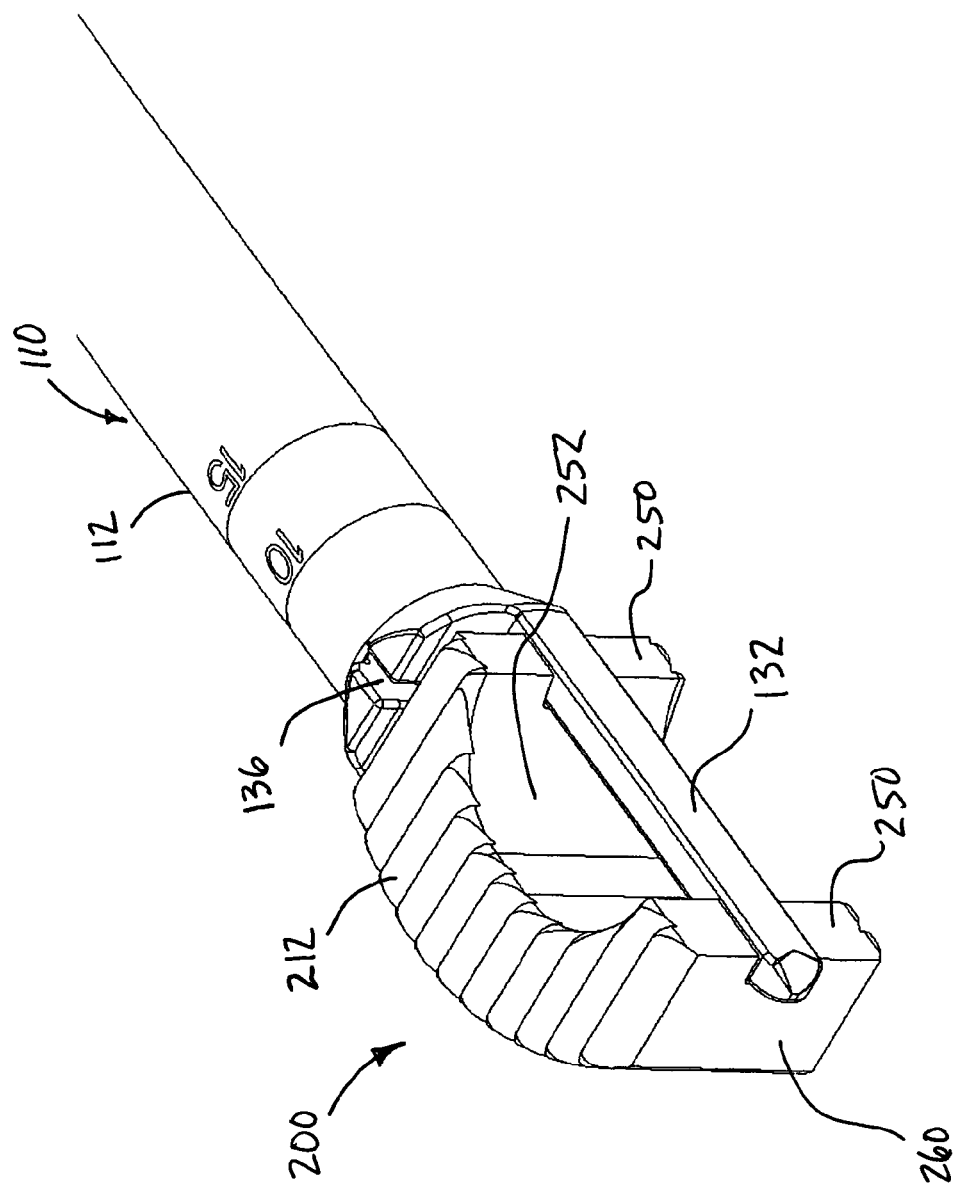
FIG. 26 is an isometric line diagram view of the exemplary 11 mm wide implant insertion tool distal end gripping an exemplary 11 mm wide, 20 mm long implant in accordance with the present invention.
Figure 27:
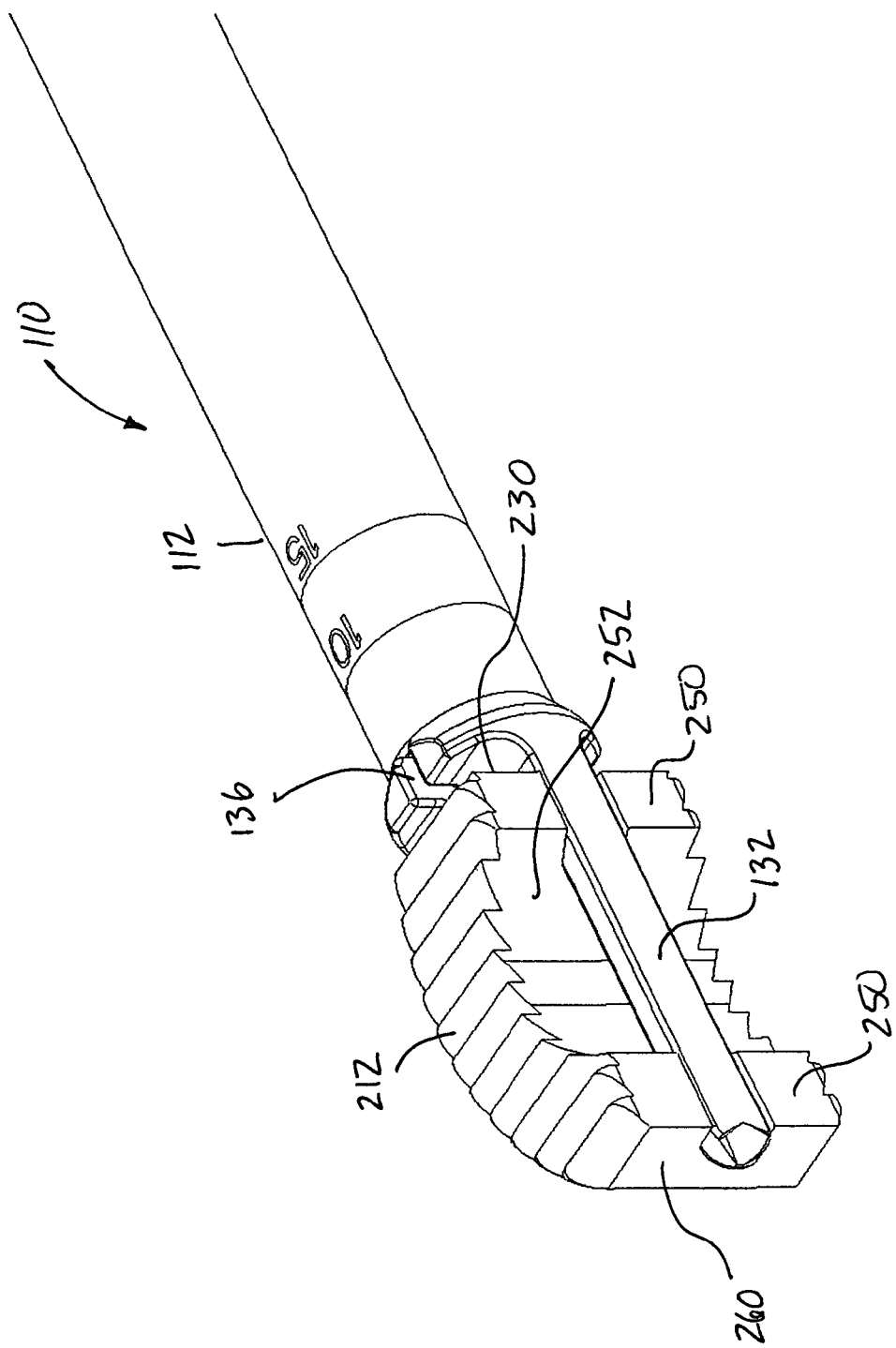
FIG. 27 is an isometric line diagram of the exemplary 9 mm wide implant insertion tool distal end gripping an exemplary 9 mm wide, 20 mm long implant in accordance with the present invention.
Figure 28:
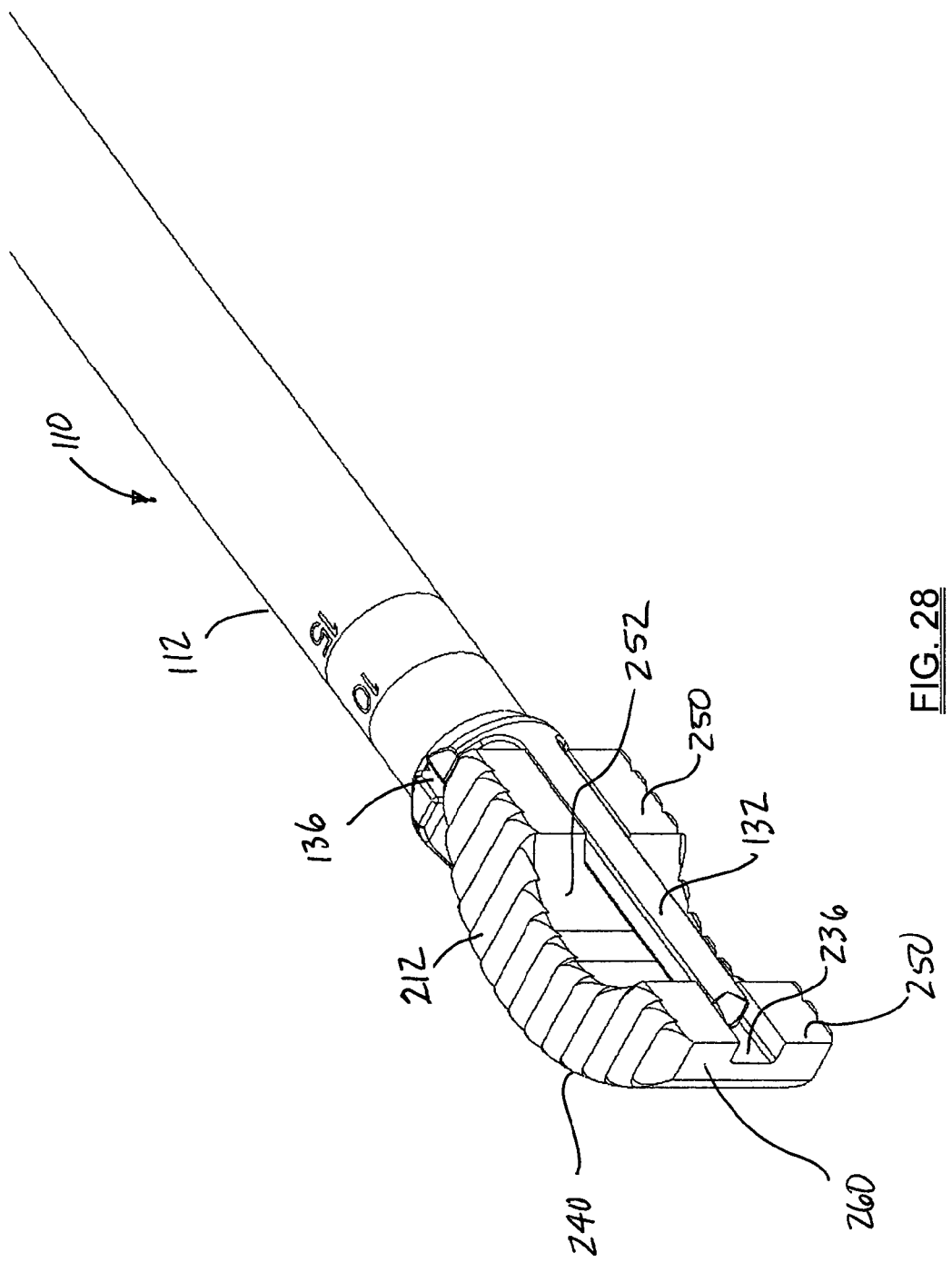
FIG. 28 is an isometric line diagram of the exemplary 9 mm wide implant insertion tool distal end gripping an exemplary 9 mm wide, 25 mm long implant in accordance with the present invention.
Figure 29:
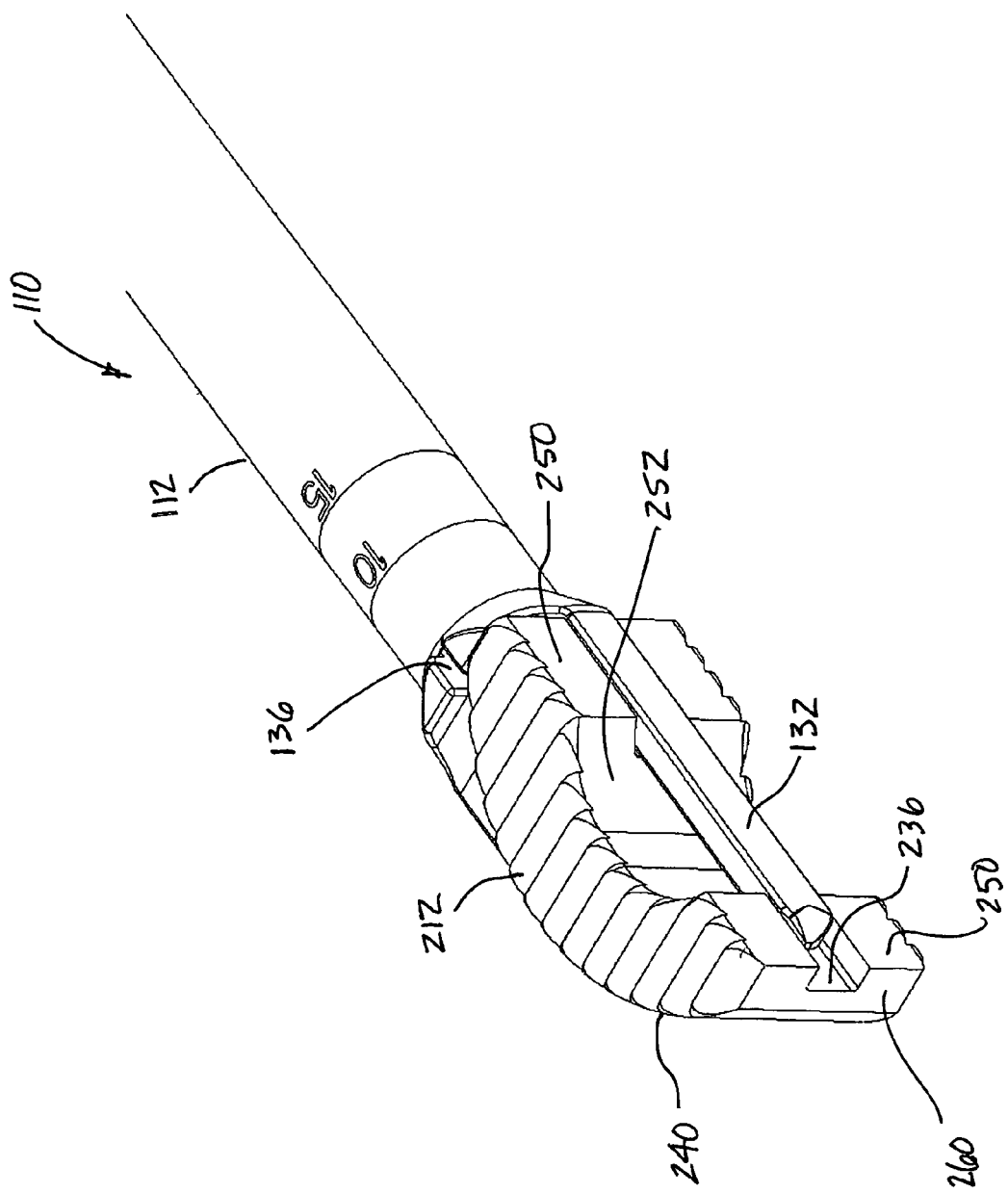
FIG. 29 is an isometric line diagram of the exemplary 11 mm wide implant insertion tool distal end gripping an exemplary 11 mm wide, 25 mm long implant in accordance with the present invention.

FIGS. 26 to 29 are diagrams of the exemplary 9 and 11 mm wide implant inserter 100 gripping one of the 20 mm and 25 mm long implants 200. FIG. 26 is an isometric drawing (line) of the exemplary 11 mm wide implant inserter 100 gripping an exemplary 20 mm long implant 200. As shown in these figures, the upper prong 132 extends beyond implant end 260. FIG. 27 is an isometric drawing (line) of the exemplary 9 mm wide implant inserter 100 gripping an exemplary 20 mm long implant 200. FIG. 28 is an isometric drawing (line) of the exemplary 9 mm wide implant inserter 100 gripping an exemplary 25 mm long implant 200. As shown in these figures, the implant end 260 extends slightly beyond the upper prong 132. FIG. 29 is an isometric drawing (line) of the exemplary 11 mm wide implant inserter 100 gripping an exemplary 25 mm long implant 200.

While this invention has been described in terms of a best mode for achieving this invention's objectives, it will be appreciated by those skilled in the art that variations may be accomplished in view of these teachings without deviating from the spirit or scope of the present invention.

What is claimed is:

1. A spinal implant for use with an inserter having a distal engagement region with a pair of prong elements in a generally parallel relationship, comprising:
a generally crescent-shaped article of bone having an outer perimeter defined by a distal end, a proximal end, a generally convex side extending between said distal and proximal ends, and a generally concave side extending between said distal and proximal ends and opposite from said convex side, the article further including a first bone-engaging surface, a second bone-engaging surface, a generally planar surface at said proximal end extending between said convex side, concave side, first bone-engaging surface, and second bone-engaging surface, and a generally U-shaped recess extending continuously around said outer perimeter through a first region comprising a substantial portion of said convex side, a second region comprising substantially the length of said generally planar surface, and a third region comprising at least a portion of said concave side, wherein said generally U-shaped recess further includes an angular offset extending between said second region and said third region.

2. The spinal implant of claim 1 and further, wherein said first and second bone-engaging surfaces include anti-migration features.

3. The spinal implant of claim 2 and further, wherein said anti-migration features on said first and second bone-engaging surfaces comprise teeth for engaging said first and second vertebral bodies.

4. The spinal implant of claim 3 and further, wherein said teeth each include a first surface and a second surface at an angle to one another.

5. The spinal implant of claim 4 and further, wherein said angle is approximately sixty degrees.

6. The spinal implant of claim 4 and further, wherein said first surface is approximately vertical and said second surface extends angularly away from said first surface.

7. The spinal implant of claim 1 and further, wherein said generally crescent-shaped article of bone has a height of up to 16 millimeters.

8. The spinal implant of claim 1 and further, wherein said generally crescent-shaped article of bone has a width of up to 11 millimeters.

9. The spinal implant of claim 1 and further, wherein said generally crescent-shaped article of bone has a length of up to 25 millimeters.

10. The spinal implant of claim 1 and further, wherein said distal end is generally flat.

11. The spinal implant of claim 1 and further, wherein the position of said generally crescent-shaped article of bone may be monitored during insertion into an intervertebral space by fluoroscopically observing said prongs of said inserter engaged within said generally U-shaped recess.

12. The implant of claim 1, wherein each of said first, second and third regions are adapted to receive at least one of a prong element of an inserter and a distal engagement region of an inserter.

13. The implant of claim 1, wherein said angular offset comprises a 45-degree offset between said second region and said third region.

14. The implant of claim 1, wherein said generally U-shaped recess further includes an angular offset extending between said second region and first region.

15. An implant for use in spinal surgery, comprising:
an article of bone having an upper bone-engaging surface for engaging a first vertebral body, a lower bone-engaging surface for engaging a second vertebral body, and an outer perimeter defined by a distal end extending between said upper and lower bone-engaging surfaces, a proximal end extending between said upper and lower bone-engaging surfaces, and first and second side surfaces extending between said upper and lower bone-engaging surfaces and between said distal and proximal ends, the article further including a generally U-shaped recess extending continuously around said outer perimeter through a first region comprising a substantial portion of said first side surface, a second region comprising substantially the length of said proximal end, and a third region comprising at least a portion of said second side surface, said proximal end comprising a generally planar surface extending between said first and second side surfaces and between said upper and lower bone-engaging surfaces, wherein said generally U-shaped recess further includes an angular offset extending between said second region and said third region.

16. The implant of claim 15 and further, wherein said first side surface is generally convex.

17. The implant of claim 15 and further, wherein said second side surface of generally concave.

18. The implant of claim 15 and further, wherein at least one of said upper and lower bone-engaging surfaces include anti-migration features for engaging said first and second vertebral bodies.

19. The implant of claim 18 and further, wherein said anti-migration features comprise teeth having a first surface and a second surface at an angle to one another.

20. The implant of claim 19 and further, wherein said angle is approximately sixty degrees.

21. The implant of claim 20 and further, wherein said first surface is approximately vertical and said second surface extends angularly away from said first surface.

22. The implant of claim 15 and further, wherein said article of bone has a height between said upper and lower bone-engaging surfaces of up to 16 millimeters.

23. The implant of claim 15 and further, wherein said article of bone has a width extending between said first and second side surfaces of up to 11 millimeters.

24. The implant of claim 15 and further, wherein said article of bone has a length extending between a proximal end and a distal end of up to 25 millimeters.

25. The implant of claim 24 and further, wherein said distal end is generally flat.

26. The implant of claim 15 and further, wherein the position of said article of bone may be monitored during insertion into an intervertebral space by fluoroscopically observing prongs of an inserter disposed within said generally U-shaped recess.

27. The implant of claim 15, wherein each of said first, second and third regions are adapted to engage at least one of a prong element of an inserter and a distal engagement region of an inserter.

28. The implant of claim 15, wherein said angular offset comprises a 45-degree offset between said second region and said third region.

29. The implant of claim 15, wherein said generally U-shaped recess further includes an angular offset extending between said second region and first region.

* * * * *